(12) United States Patent
Wu et al.

(10) Patent No.: US 9,211,411 B2
(45) Date of Patent: Dec. 15, 2015

(54) THERAPY FOR RAPID EYE MOVEMENT BEHAVIOR DISORDER (RBD)

(75) Inventors: Jianping Wu, Shoreview, MN (US); Dwight E. Nelson, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 391 days.

(21) Appl. No.: 13/211,904

(22) Filed: Aug. 17, 2011

(65) Prior Publication Data
US 2012/0053508 A1 Mar. 1, 2012

Related U.S. Application Data

(60) Provisional application No. 61/377,367, filed on Aug. 26, 2010.

(51) Int. Cl.
| | | |
|---|---|---|
| *A61N 1/36* | (2006.01) |
| *A61B 5/04* | (2006.01) |
| *A61B 5/0476* | (2006.01) |
| *A61B 5/00* | (2006.01) |
| *A61B 5/11* | (2006.01) |
| *A61B 5/0488* | (2006.01) |

(52) U.S. Cl.
CPC ........ *A61N 1/36067* (2013.01); *A61B 5/04001* (2013.01); *A61B 5/0476* (2013.01); *A61B 5/4812* (2013.01); *A61B 5/4815* (2013.01); *A61B 5/6868* (2013.01); *A61N 1/36078* (2013.01); *A61B 5/0488* (2013.01); *A61B 5/1104* (2013.01); *A61B 5/1116* (2013.01); *A61B 5/4836* (2013.01); *A61B 2562/0219* (2013.01); *A61N 1/36003* (2013.01)

(58) Field of Classification Search
USPC .................................................... 607/48, 2
See application file for complete search history.

(56) References Cited

U.S. PATENT DOCUMENTS

| | | |
|---|---|---|
| 4,013,068 A | 3/1977 | Settle et al. |
| 4,138,649 A | 2/1979 | Schaffer |
| 4,279,258 A | 7/1981 | John |
| 4,579,125 A | 4/1986 | Strobl et al. |
| 4,610,259 A | 9/1986 | Cohen et al. |

(Continued)

FOREIGN PATENT DOCUMENTS

| | | |
|---|---|---|
| CN | 2754557 Y | 2/2006 |
| CN | 10199670 A | 1/2008 |

(Continued)

OTHER PUBLICATIONS

Neagu et al. "PPN Evoked Potentials During STN Stimulation of Parkinson's Disease Patients," Presentation Abstract, 40th Annual Meeting Neuroscience, Nov. 16, 2010, p. 1-2.

(Continued)

*Primary Examiner* — Paula J Stice
(74) *Attorney, Agent, or Firm* — Shumaker & Sieffert, P.A.

(57) ABSTRACT

Examples for delivering electrical stimulation to a patient via a medical device to manage or treat rapid eye movement behavior disorder (RBD) are described. In one example, a method comprises determining a patient is in a rapid eye movement (REM) sleep stage, and delivering electrical stimulation therapy to the patient based on the determination that the patient is in the REM sleep stage, where the electrical stimulation therapy is delivered to inhibit movement of the patient during the REM sleep stage. In some examples, the electrical stimulation therapy may be delivered to the brain of the patient.

34 Claims, 7 Drawing Sheets

(56) References Cited

U.S. PATENT DOCUMENTS

| | | | |
|---|---|---|---|
| 4,776,345 A | | 10/1988 | Cohen et al. |
| 5,206,602 A | | 4/1993 | Baumgartner et al. |
| 5,215,086 A | * | 6/1993 | Terry et al. .................. 607/46 |
| 5,299,569 A | * | 4/1994 | Wernicke et al. ............ 607/45 |
| 5,335,657 A | * | 8/1994 | Terry et al. .................. 607/45 |
| 5,458,117 A | | 10/1995 | Chamoun et al. |
| 5,619,536 A | | 4/1997 | Gourgue |
| 5,725,558 A | | 3/1998 | Warnke |
| 5,769,877 A | | 6/1998 | Barreras, Sr. |
| 5,833,709 A | | 11/1998 | Rise et al. |
| 5,840,040 A | | 11/1998 | Altschuler et al. |
| 6,011,990 A | | 1/2000 | Schultz et al. |
| 6,018,682 A | | 1/2000 | Rise |
| 6,024,700 A | | 2/2000 | Nemirovski et al. |
| 6,094,598 A | | 7/2000 | Elsberry et al. |
| 6,129,681 A | | 10/2000 | Kuroda et al. |
| 6,157,857 A | | 12/2000 | Dimpfel |
| 6,315,740 B1 | | 11/2001 | Singh |
| 6,331,160 B1 | | 12/2001 | Bardy |
| 6,463,328 B1 | | 10/2002 | John |
| 6,468,234 B1 | | 10/2002 | Van der Loos et al. |
| 6,483,355 B1 | | 11/2002 | Lee et al. |
| 6,597,953 B2 | | 7/2003 | Boling |
| 6,605,038 B1 | | 8/2003 | Teller et al. |
| 6,876,842 B2 | | 4/2005 | Davie |
| 6,993,380 B1 | | 1/2006 | Modarres |
| 7,110,820 B2 | | 9/2006 | Tcheng et al. |
| 7,142,917 B2 | | 11/2006 | Fukui |
| 7,151,961 B1 | | 12/2006 | Whitehurst et al. |
| 7,177,609 B1 | | 2/2007 | Wong et al. |
| 7,299,088 B1 | | 11/2007 | Thakor et al. |
| 7,385,443 B1 | | 6/2008 | Denison |
| 7,684,867 B2 | | 3/2010 | Jaax et al. |
| 8,121,694 B2 | | 2/2012 | Molnar et al. |
| 8,290,596 B2 | | 10/2012 | Wei et al. |
| 8,380,314 B2 | | 2/2013 | Panken et al. |
| 2002/0002390 A1 | | 1/2002 | Fischell et al. |
| 2002/0177882 A1 | | 11/2002 | DiLorenzo |
| 2003/0046254 A1 | | 3/2003 | Ryu et al. |
| 2003/0149457 A1 | | 8/2003 | Tcheng et al. |
| 2003/0171791 A1 | | 9/2003 | KenKnight et al. |
| 2004/0002635 A1 | | 1/2004 | Hargrove et al. |
| 2004/0077967 A1 | | 4/2004 | Jordan |
| 2004/0122483 A1 | | 6/2004 | Nathan et al. |
| 2004/0158119 A1 | | 8/2004 | Osorio et al. |
| 2004/0167418 A1 | | 8/2004 | Nguyen et al. |
| 2004/0176809 A1 | | 9/2004 | Cho et al. |
| 2004/0215286 A1 | | 10/2004 | Stypulkowski |
| 2004/0249422 A1 | | 12/2004 | Gliner et al. |
| 2005/0043652 A1 | | 2/2005 | Lovett et al. |
| 2005/0065427 A1 | | 3/2005 | Magill et al. |
| 2005/0081847 A1 | | 4/2005 | Lee et al. |
| 2005/0197588 A1 | | 9/2005 | Freeberg |
| 2005/0209511 A1 | | 9/2005 | Heruth et al. |
| 2005/0209512 A1 | | 9/2005 | Heruth et al. |
| 2005/0209644 A1 | | 9/2005 | Heruth et al. |
| 2005/0216064 A1 | * | 9/2005 | Heruth et al. ................. 607/3 |
| 2005/0240242 A1 | | 10/2005 | DiLorenzo |
| 2006/0041221 A1 | | 2/2006 | Stypulkowski |
| 2006/0106275 A1 | | 5/2006 | Raniere |
| 2006/0133550 A1 | | 6/2006 | Bolton et al. |
| 2006/0135879 A1 | | 6/2006 | Liley |
| 2006/0149338 A1 | | 7/2006 | Flaherty et al. |
| 2006/0169282 A1 | | 8/2006 | Izumi et al. |
| 2006/0173494 A1 | | 8/2006 | Armstrong et al. |
| 2006/0206174 A1 | | 9/2006 | Honeycutt et al. |
| 2006/0212093 A1 | | 9/2006 | Pless et al. |
| 2006/0258930 A1 | | 11/2006 | Wu et al. |
| 2006/0259099 A1 | | 11/2006 | Goetz et al. |
| 2006/0293604 A1 | | 12/2006 | Carlson et al. |
| 2007/0010755 A1 | | 1/2007 | Sarkela et al. |
| 2007/0016095 A1 | | 1/2007 | Low et al. |
| 2007/0032737 A1 | | 2/2007 | Causevic et al. |
| 2007/0032834 A1 | | 2/2007 | Gliner et al. |
| 2007/0038265 A1 | | 2/2007 | Tcheng et al. |
| 2007/0123758 A1 | | 5/2007 | Miesel et al. |
| 2007/0150025 A1 | | 6/2007 | DiLorenzo et al. |
| 2007/0213785 A1 | | 9/2007 | Osorio et al. |
| 2008/0051839 A1 | | 2/2008 | Libbus et al. |
| 2008/0071314 A1 | | 3/2008 | John |
| 2008/0077191 A1 | | 3/2008 | Morrell |
| 2008/0154111 A1 | | 6/2008 | Wu et al. |
| 2008/0195166 A1 | | 8/2008 | Sun et al. |
| 2008/0243005 A1 | | 10/2008 | Jung et al. |
| 2008/0269812 A1 | | 10/2008 | Gerber et al. |
| 2009/0082691 A1 | | 3/2009 | Denison et al. |
| 2009/0082831 A1 | | 3/2009 | Paul et al. |
| 2009/0118786 A1 | | 5/2009 | Meadows et al. |
| 2009/0118787 A1 | | 5/2009 | Moffitt et al. |
| 2009/0131995 A1 | | 5/2009 | Sloan et al. |
| 2009/0192556 A1 | | 7/2009 | Wu et al. |
| 2009/0264789 A1 | | 10/2009 | Molnar et al. |
| 2011/0015469 A1 | | 1/2011 | Walter et al. |
| 2011/0112590 A1 | | 5/2011 | Wu et al. |
| 2012/0053508 A1 | | 3/2012 | Wu et al. |

FOREIGN PATENT DOCUMENTS

| | | |
|---|---|---|
| DE | 19649991 A | 6/1998 |
| EP | 438945 A | 7/1991 |
| EP | 789449 A2 | 8/1997 |
| EP | 2008581 A2 | 12/2008 |
| GB | 2447640 A | 9/2008 |
| JP | 2008154681 | 7/2008 |
| KR | 20010096372 | 11/2001 |
| RU | 2144310 | 1/2000 |
| WO | 2005089641 A1 | 9/2005 |
| WO | 2005089646 A1 | 9/2005 |
| WO | 2006121455 A1 | 11/2006 |
| WO | 2006126186 A1 | 11/2006 |
| WO | 2007112092 A2 | 10/2007 |
| WO | 2009039294 A1 | 3/2009 |
| WO | 2009042170 A1 | 4/2009 |
| WO | 2009059041 A1 | 5/2009 |

OTHER PUBLICATIONS

Lai et al. "Muscle Tone Suppression and Stepping Produced by Stimulation of Midbrain and Rostral Pontine Reticular Formation" The Journal of Neuroscience, Aug. 1990, 10(8): p. 2727-2734.

International Search Report and Written Opinion for corresponding PCT Application No. PCT/US2011/048663, (15 pgs.).

Academic Press Dictionary of Science and Technology, definition of "baseband" Oxford: Elsevier Science and Technology, 1992, 2 pp. (Applicant points out that, in accordance with MPEP 609.04(a), the 1992 year of publication is sufficiently earlier than the effective U.S. filing date and any foreign priority date so that the particular month of publication is not in issue.).

Authorative Dictionary of IEEE Standar Terms (Seventh Edition), definition of "baseband" pp. 86, New York: IEEE, 2000, 3 pp. (Applicant points out that, in accordance with MPEP 609.04(a), the 2000 year of publication is sufficiently earlier than the effective U.S. filing date and any foreign priority date so that the particular month of publication is not in issue.).

Rauscher, et al., "Practical Realization of an Analyzer Operating on the Heterodyne Principle," Chapter 4 (partial) of Fundamentals of Spectrum Analysis, Rohde & Schwarz, 2001, pp. 34-64 (Applicant points out that, in accordance with MPEP 609.04(a), the 2000 year of publication is sufficiently earlier than the effective U.S. filing date and any foreign priority date so that the particular month of publication is not in issue.).

Rudell, et al. "Recent Developments in High Integration Multi-Standard CMOS Transceivers for Personal Communication Systems," published in 1998 International Symposium on Low Power Electronics and Design, Aug. 1998, pp. 149-154, 6 pp.

Jianpin et al., "Study on Feature Extraction of the Sleep-Multigraphy," Journal of Biomedical Engineering, Issue 5, vol. 22, pp. 906-909, Dec. 2005, translation of abstract and portions mentioned in the First Office Action from SIPO in Counterpart Chinese Application nu. 200801256111.1.

(56) References Cited

OTHER PUBLICATIONS

Masui, "A 0.6 V Supply CMOS Amplifier Using Noise Reduction Technique of Autozeroing and Chopper Stabilization," 21st Century COE Program, Hiroshima University, Proceedings of the Fifth Hiroshima International Workshop, Jan. 29-30, 2007, 5 pp.

Foffani, et al., "Analysis of local field potentials from the human subthalamic nucleus," Proceedings of the 25th Annual International Conference of the IEEE EMBS, Sep. 17-21, 2003, 3 pp.

U.S. Appl. No. 60/999,097, filed Oct. 16, 2007, entitled, "Frequence Selective Monitoring of Physiological Signals".

U.S. Appl. No. 60/975,372, filed Sep. 26, 2007, entitled "Patient Directed Therapy Control".

U.S. Appl. No. 61/025,503, filed Feb. 1, 2008, entitled "Frequency Selective Monitoring of Physiological Signals".

U.S. Appl. No. 61/083,381, filed Jul. 24, 2008, entitled "Frequency Selective Monitoring of Physiological Signals".

Prosecution History from U.S. Appl. No. 12/238,105, dated Jan. 26, 2012 through Apr. 22, 2014, 170 pp.

Final Office Action from U.S. Appl. No. 12/238,105, dated Jul. 2, 2014, 15 pp.

Amendment in Response to Office Action dated Jul. 2, 2014, from U.S. Appl. No. 12/238,105, filed Oct. 2, 2014, 19 pp.

Notice of Allowance from U.S. Appl. No. 12/238,105, dated Feb. 25, 2015, 10 pp.

* cited by examiner

THERAPY FOR RAPID EYE MOVEMENT BEHAVIOR DISORDER (RBD)

This application claims the benefit of U.S. Provisional Application Ser. No. 61/377,367, to Wu et al., filed Aug. 26, 2010, and entitled "THERAPY FOR RAPID EYE MOVEMENT BEHAVIOR (RBD) DISORDER," which is incorporated herein by reference in its entirety.

TECHNICAL FIELD

The disclosure relates to medical therapy systems, and, more particularly, control of medical therapy systems.

BACKGROUND

In some cases, an ailment or medical condition may affect the quality of a patient's sleep. For example, neurological disorders may cause a patient to have difficulty falling asleep, and may disturb the patient's sleep, e.g., cause the patient to wake frequently during the night and/or early in the morning. Further, neurological disorders may cause the patient to have difficulty achieving deep sleep stages.

Examples of neurological disorders that may negatively affect patient sleep quality include movement disorders, such as tremor, Parkinson's disease, multiple sclerosis, or spasticity. Other examples of neurological disorders that may negatively affect patient sleep quality include sleep disorders, such as, rapid eye movement behavior disorder (RBD), in which case, a patient may act out dramatic and/or violent dreams, shout or make other noises (e.g., grunting) during the rapid eye movement (REM) sleep. In each case, the uncontrolled movement associated with such sleep and movement disorders may cause a patient to have difficulty falling asleep, disturb the patient's sleep or that of a sleep partner, or cause the patient to have difficulty achieving or maintaining deep sleep stages. In case of RBD, for example, a patient can cause injury to themselves or others.

Drugs are often used to treat neurological disorders. In some cases, neurological disorders are treated via an implantable medical device (IMD), such as an implantable stimulator or drug delivery device. In some examples, the treatments for neurological disorders may themselves affect sleep quality. Further, in some cases, poor sleep quality may increase the symptoms experienced by a patient. The condition of a patient with such an ailment may progressively worsen when symptoms disturb sleep quality, which may, in turn, increase the frequency and/or intensity of symptoms of the patient's condition.

SUMMARY

In general, the disclosure is directed to systems, devices, and techniques for delivering therapy such as electrical stimulation therapy to the brain of a patient to treat or manage rapid eye movement behavior disorder (RBD). In some examples, a medical device system, including an implantable medical device (IMD) or other medical device, may determine when a patient is in a rapid eye movement (REM) sleep stage. For example, the medical device system may monitor one or more biosignals indicative of activity within the brain of the patient, and detect when the patient is in an REM sleep based on the biosignal of the patient. Based on the determination that the patient is in an REM sleep stage, the medical device system may then deliver electrical stimulation therapy to the patient, e.g., to the brain of the patient.

In some examples, the therapy may be delivered to the patient in a manner that inhibits movement of the patient, e.g., body, limb, hand, foot or other movement, during the REM sleep stage. By inhibiting movement of the patient during the REM sleep stage via delivery of electrical stimulation to the patient, the uncontrolled physical movement of the patient during the REM sleep stage associated with RBD may be reduced or even eliminated entirely. In this manner, the medical device system may treat or manage RBD by delivering therapy to a patient when a patient is in an REM sleep stage.

In one aspect, the disclosure is directed to a method comprising determining a patient is in a rapid eye movement (REM) sleep stage; and delivering therapy to the patient based on the determination that the patient is in the REM sleep stage, wherein the therapy is delivered to the brain to inhibit movement of the patient during the REM sleep stage.

In another aspect, the disclosure is directed to a system comprising a therapy module, and a processor that determines the patient is in a REM sleep stage and controls the therapy module to deliver therapy to the patient, wherein the therapy is delivered to the brain to inhibit patient movement.

In another aspect, the disclosure is directed to a system comprising means for determining a patient is in a rapid eye movement (REM) sleep stage; and means for delivering therapy to the patient based on the determination that the patient is in the REM sleep stage, wherein the electrical stimulation therapy is delivered to inhibit patient movement.

In another aspect, the disclosure is directed to a non-transitory computer-readable storage medium comprising instructions that cause a programmable processor to determine a patient is in a rapid eye movement (REM) sleep stage; and control a therapy module to deliver therapy to the patient based on the determination that the patient is in the REM sleep stage, wherein the electrical stimulation therapy is delivered to inhibit patient movement.

In another aspect, the disclosure is directed to a non-transitory computer-readable storage medium comprising instructions. The instructions cause a programmable processor to perform any part of the techniques described herein. The instructions may be, for example, software instructions, such as those used to define a software or computer program. The computer-readable medium may be a computer-readable storage medium such as a storage device (e.g., a disk drive, or an optical drive), memory (e.g., a Flash memory, random access memory or RAM) or any other type of volatile or non-volatile memory that stores instructions (e.g., in the form of a computer program or other executable) to cause a programmable processor to perform the techniques described herein.

The details of one or more examples of the disclosure are set forth in the accompanying drawings and the description below. Other features, objects, and advantages of the systems, methods, and devices in accordance with the disclosure will be apparent from the description and drawings, and from the claims.

DETAILED DESCRIPTION

Figure 1:
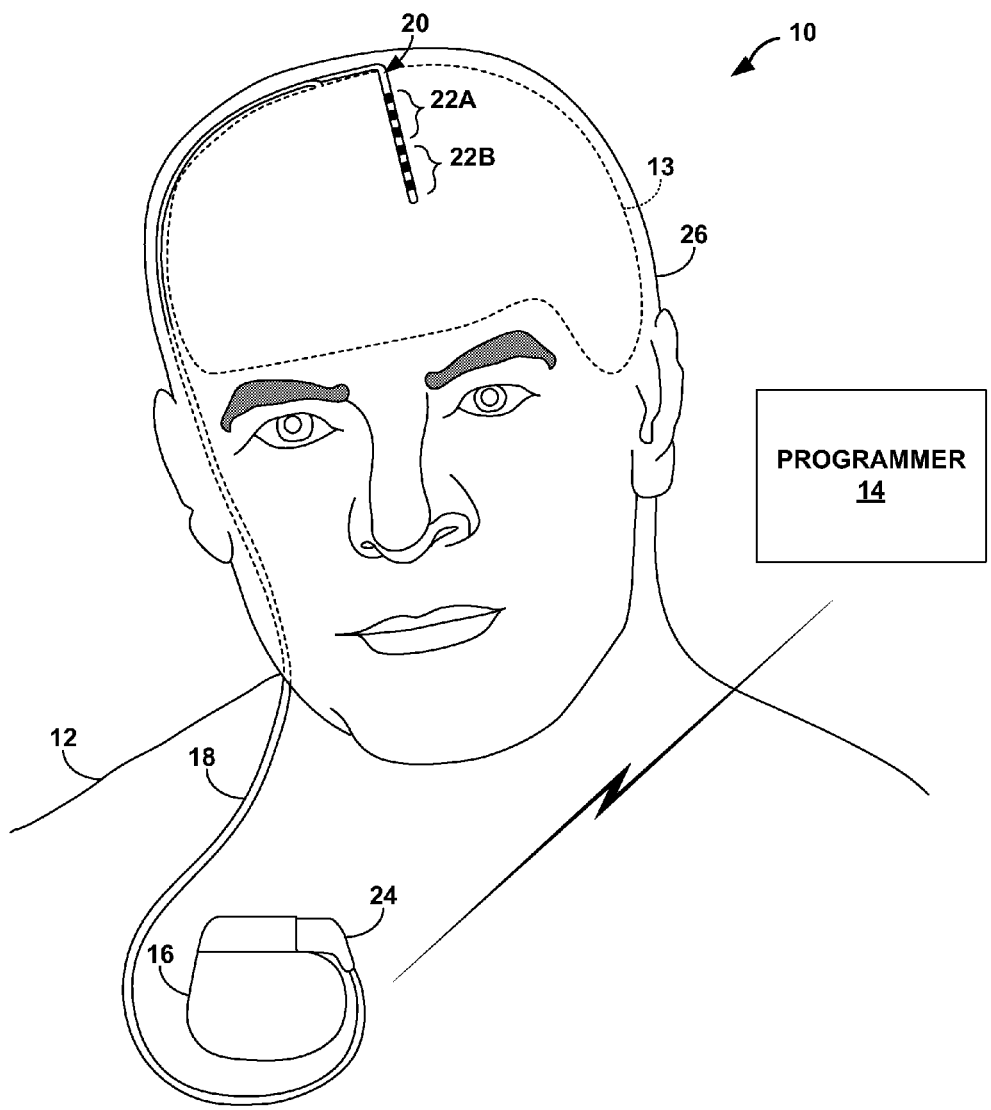
FIG. 1 is a conceptual diagram illustrating an example deep brain stimulation (DBS) system.

In general, the disclosure is directed to systems, devices, and techniques for delivering therapy such as electrical stimulation therapy to a patient to treat or manage rapid eye movement behavior disorder (RBD). For example, electrical stimulation therapy may be delivered to a patient to treat or manage RBD by managing the outward physical symptoms such as movement generally attendant to RBD when the patient is in a REM sleep stage. For ease of illustration, examples of the disclosure are primarily described with regard to the delivery of therapy in the form of electrical stimulation therapy delivered to the brain of a patient to treat or manage RBD. However, as will be described below, examples are not limited to the delivery of electrical stimulation to the brain of the patient but may additionally or alternatively include the delivery of electrical stimulation to other tissue sites of a patient and/or the delivery of a therapeutic agent to patient to treat or manage RBD.

In some examples, a medical device system including an implantable medical device (IMD) or other medical device, may determine when a patient is in a rapid eye movement (REM) sleep stage. For example, the medical device system may monitor one or more biosignals indicative of the activity within the brain of the patient, and detect when the patient is in an REM sleep based on the biosignal of the patient. Based on the determination that the patient is in an REM sleep stage, the medical device system may then deliver electrical stimulation therapy to the patient.

The electrical stimulation therapy may be delivered to the patient in a manner that inhibits the movement of the patient during the REM sleep stage. By inhibiting the movement of the patient during the REM sleep stage via delivery of electrical stimulation to the brain of the patient, the uncontrolled physical movement of the patient during the REM sleep stage associated with RBD may be at least partially reduced or even eliminated entirely. In this manner, the medical device system may treat or manage RBD by delivering therapy to a patient, e.g., when a patient is in an REM sleep stage.

As described above, in some cases, a patient's ability to sleep or quality of sleep may be affected by symptoms of RDB. In general, for patients not having RBD, during REM sleep stages, the patient may experience REM atonia, in which the motor neurons of the brain are not stimulated and, thus, the muscle in the body of the patient do not move or movement is significantly inhibited. However, such lack of movement during REM sleeps stages may not be experienced by patients with RBD. RBD is a sleep disorder that may occur when there is a loss of normal voluntary muscle atonia (or REM atonia) during REM sleep stage. The loss of normal voluntary muscle atonia may cause abnormal behavior of the patient while the patient is in a REM sleep stage. In some examples, the loss of REM atonia may cause the patient to experience uncontrolled physical movement while in a REM sleep stage, including motor behavior that is in response to dream content. This general loss of motor inhibition may cause the patient in some cases to act out physically in an undesired manner. In some cases, the undesired physical movement may be relatively violent, which can disturb, or even result in injury to, the patient or bed partner.

According to techniques described herein, an IMD or other medical device may deliver electrical stimulation therapy to the brain of patient based on the determination that a patient is in a REM sleep stage to treat RBD. The electrical stimulation therapy may be delivered to the brain of the patient in a manner that inhibits movement of the patient during REM sleep stage. In general, the delivery of the electrical stimulation therapy to the brain of the patient may reduce the uncontrolled physical movement of the patient associated with RBD to treat the symptoms of RBD experienced by the patient.

Inhibiting the movement of the patient may include at least partially reducing or eliminating the physical movement of patient, e.g., as compared to the movement that would be exhibited by the patient during a REM sleep state due to RBD when not treated by therapy. The therapy delivered to the patient may inhibit physical movements of the patient that are symptomatic of RBD. Symptomatic physical movements of RBD may include the coordinated physical movement of one or more limbs of the patient, which may include kicking, punching, thrashing, and/or other coordinated movement of the patient. In some examples, the movement inhibited by the therapy delivered to the patient may include relatively high amplitude physical movement having a relatively rapid onset movement.

Such symptomatic physical movements may be reduced or substantially eliminated via the delivery of therapy to the patient. Reduction of symptomatic physical movement may include a reduction in frequency and/or amplitude of the patient movement, or frequency of episodes of patient movement. In some examples, substantially all physical movement of a patient may be eliminated by the delivery of therapy to the patient. However, in some examples, some physical movement may be present despite the delivery of therapy to patient to treat RBD. For example, movement generally associated with REM sleep for patients not having RBD, such as, e.g., high frequency eye movement, may be exhibited. In some instances, movement symptomatic of another movement disorder of the patient other than that of RBD may be exhibited during the delivery of therapy to treat RBD. For example, for a patient having Parkinson's disease, tremors, which may be characterized as low amplitude, high frequency movement, may be experience during REM sleep despite the delivery of therapy to the patient to treat RBD. As another example, for a patient having periodic limb movement disorder (PLMD), repetitive cramping or jerking of the legs or other movement from PLMD may be experienced during REM sleep despite the delivery of therapy to the patient to treat RBD. In the case of PLMD, "periodic" may refer to the fact that the movements during sleep are repetitive and rhythmic, occurring every 20-40 seconds, for example. In still other examples, substantially all limb movement of a patient may be prevented by the delivery of therapy to the patient to treat RBD.

Some examples of the disclosure include the delivery of therapy to the patient in the form of electrical stimulation therapy to treat or manage RBD. For ease of illustration, examples of the disclosure are primarily described with regard to the delivery of electrical stimulation to one or more tissue sites in the brain of a patient. Other types of electrical stimulation therapy are contemplated, such as, e.g., the delivery of electrical stimulation to a nerve site and/or muscle tissue in the patient. Additionally or alternatively, examples may include delivery of one or more therapeutic agents to the patient. In each case, the therapy delivered to the patient may treat or manage RBD as described in the disclosure.

In some examples, physical movement of the patient may be inhibited by delivery of electrical stimulation therapy that causes rigidity in the patient to effectively hold the body of a patient still while the patient is in a REM sleep stage. In some examples, movement of a patient may be inhibited by the delivery of electrical stimulation therapy that temporarily causes atonia in the patient to prevent physical movement of the patient. In some examples, movement of a patient may be inhibited by the delivery of electrical stimulation therapy that relaxes the muscle tone of patient to prevent motor activity of the patient while in a REM sleep stage. In still other examples, movement of a patient may be inhibited by the delivery of electrical stimulation therapy to cause the patient to experience akinesia. In each case, the electrical stimulation therapy delivered to the patient may prevent the patient from experiencing the undesired physical movements associated with RBD while the patient is in a REM sleep stage.

In some examples, the electrical stimulation may be delivered to the brain of a patient by an IMD or other medical device via one or more electrodes implanted within the brain of the patient. The electrical stimulation therapy may be delivered by an IMD via the implanted electrode(s) to the brain of the patient while in a REM sleep stage, and may deliver the stimulation to a single target tissue site or multiple target tissue sites. As will be described below, in some examples, the electrical stimulation may be delivered to the globus pallidus pars interna (GPi), subthalamic nucleus (STN) and/or other basal ganglia (e.g., striatum, pallidum, substantia nigra) of a patient may help manage symptoms of the movement disorder of the patient. For example, an IMD or other medical device may deliver electrical stimulation to such target sites to cause rigidity in the patient. In some examples, electrical stimulation may be delivered to one or more midbrain sites. Example midbrain sites may include midbrain nuclei, such as, e.g., midbrain retrorubral (RRN), ventral paralemniscal tegmental field (vFTP), reticular tegmental (TRN), and pedunculopontine tegmental (PPN) nuclei. In some examples, an IMD or other medical device may deliver electrical stimulation to such target sites to relax the muscle tone of the patient to prevent patient movement while the patient is in a REM sleep stage. Other target tissue sites of the brain are contemplated.

The influence of the electrical stimulation delivered to the patient may vary based on the target stimulation site as well as the electrical stimulation parameters that define the stimulation therapy delivered to the patient. Parameters of the electrical stimulation may include voltage amplitude or current amplitude, pulse frequency, pulse width, electrode combination, and electrode polarity. In each case, the electrical stimulation therapy may be delivered to the brain of the patient in a manner that treats RBD by reducing the undesired physical movements experienced by the patient with RBD during a REM sleep stage.

In some examples, an IMD or other medical device may also treat one or more other patient neurological conditions besides that of RBD, i.e., in addition to RBD, via delivery of electrical stimulation therapy. In other words, the IMD may be configured to delivery therapy to alleviate symptoms of other disorders in addition to RBD. For example, an IMD may deliver electrical stimulation therapy via one or more electrodes implanted in the brain of a patient to treat a movement disorder such as tremor, Parkinson's disease (PD), multiple sclerosis, or spasticity. There may be a correlation between REM behavior disorder and the onset of a movement disorder (e.g., Parkinson's disease), although the exact correlation is unknown. In some examples, a medical device system may help to manage sleep disorder symptoms of patients with conditions other than neurological conditions, such as psychiatric (or psychological) disorders. Examples of psychiatric disorders may include major depressive disorder, anxiety, hypomania or bipolar disorder. The electrical stimulation therapy to treat or manage these other patient conditions may be delivered to the same or different regions of the brain of the patient with the same or different stimulation parameters.

A patient may be determined to be in a REM sleep stage based on a biosignal that is indicative of activity within the brain of the patient. Examples of biosignals indicative of activity within a brain of a patient include, but are not limited to, bioelectrical brain signals, such as electrical signals generated from local field potentials (LFPs) within one or more regions of brain 13, an electroencephalogram (EEG) signal and/or an electrocorticogram (ECoG) signal. In some examples, the electrical signals within the brain of the patient may reflect changes in electrical current produced by the sum of electrical potential differences across brain tissue. Such biosignals may be monitored by an IMD or other medical device and analyzed to detect when a patient occupies a REM sleep stage. Patient biosignals may be monitored via implanted and/or external electrodes and may be analyzed via one or more processors of an implanted and/or external medical device.

In some examples, an IMD or other medical device may monitor one or more physiological parameters of a patient which are indicative of the patient being in a REM sleep stage to detect when patient is in a REM sleep stage, e.g., in combination with the monitored biosignals of the patient. Suitable patient physiological parameters may include, but are not limited to, muscle tone (e.g., as sensed via electromyography (EMG)), eye movement (e.g., as sensed via electroculography (EOG) or EEG), and body temperature. In some examples, patient movement may be monitored via actigraphy.

In one example, an IMD or other medical device may monitor an EMG signal reflective of the muscle tone of a patient to identify physical movement of the patient. Alternatively or additionally, an IMD or other medical device may monitor the physical movement of a patient via one or more motion sensors, such as, e.g., one or more single or multi-axis accelerometer devices. In some examples, the physical movement and/or muscle tone of a patient may be monitored in conjunction with the delivery of electrical stimulation therapy to help determine the effectiveness of the therapy being delivered to the patient in inhibiting patient movement during a REM sleep stage. In such a case, if an undesired level of patient physical movement is detected while a patient is receiving therapy to treat RBD, then the therapy being delivered to the patient may be adjusted, e.g., by adjusting the stimulation location in the brain and/or adjusting the value of one or more stimulation therapy parameters.

Additionally or alternatively, an IMD or other medical device may be configured such that the delivery of movement inhibiting therapy to treat RBD is initiated upon detection of physical movement of the patient in combination with the sensing of biosignals that are indicative of the patient being in a REM sleep stage. For example, upon detecting one or more biosignals indicative of the patient being in a REM sleep stage, an IMD may wait to initiate delivery of therapy for treatment of RBD until physical movement of the patient is detected. In other examples, an IMD may initiate the delivery of therapy substantially immediately or after some programmed time delay upon determining that a patient is in a REM sleep stage based on sensed biosignals of the patient. An IMD or other medical device may monitor for instances of a patient being in a REM sleep stage on a substantially continuous or periodic (e.g., only during selected time periods during a 24 hour period) basis.

FIG. 1 is a conceptual diagram illustrating an example deep brain stimulation (DBS) system 10 that manages a medical condition of patient 12, such as a neurological disorder. Example neurological disorders that DBS system may be useful for managing include sleep disorders, such as, e.g., RBD. Patient 12 ordinarily will be a human patient. In some cases, however, DBS system 10 may be applied to other mammalian or non-mammalian non-human patients. DBS system 10 may provide therapy to patient 12 in order to minimize the severity or duration of one or more patient conditions, and, in some cases, in order to eliminate symptoms associated with the patient condition, including RBD. DBS system 10 includes medical device programmer 14, implantable medical device (IMD) 16, lead extension 18, and lead 20 with respective electrodes 22A and 22B (collectively referred to as "electrodes 22"). For ease of description examples of the disclosure are primarily described with regard to DBS system 10. However, examples of the disclosure are not limited as such, but may include any medical system or device suitable for implementing one or more of the examples techniques described in this disclosure for treating RBD.

IMD 16 of system 10 includes a therapy module that delivers electrical stimulation therapy to one or more regions of brain 13 via lead 20. In the example shown in FIG. 1, system 10 may be referred to as a deep brain stimulation (DBS) system because IMD 16 provides electrical stimulation therapy directly to tissue within brain 13, such as under the dura mater of brain 13. In addition to or instead of deep brain sites, IMD 16 may deliver electrical stimulation to target tissue sites on a surface of brain 13, such as between the patient's cranium and the dura mater of brain 13 (e.g., the cortical surface of brain 13).

As described above, some examples of the disclosure may include the delivery of electrical stimulation therapy to patient 12 to inhibit (e.g., reduce or prevent) the physical movement of patient 12 associated with RBD when patient 12 is determined to be in a REM sleep stage. For ease of illustration, examples of the disclosure are primarily described with regard to the delivery of such electrical stimulation therapy to brain 13 of patient 12 by IMD 16. However, in other examples, an IMD or other medical device may deliver electrical stimulation therapy other than that of brain stimulation may be delivered to patient 12 to inhibit the physical movement of patient 12 as described herein in addition to or instead of the brain stimulation. For example, in some cases, IMD 16 may deliver stimulation to one or more nerve sites and/or one more muscle sites on or in patient 12. In some examples, IMD 16 may deliver spinal cord stimulation (SCS) to patient 12, e.g., via one or more leads implanted adjacent the spinal cord of patient 12, in manner that inhibits patient movement associated with RBD. The electrical stimulation may be delivered to ventral (anterior) sites to block motor or disrupt motor output from the spinal cord (not shown) of patient 12, e.g., to disrupt the limb movement of patient 12. Additionally or alternatively, IMD 16 may deliver electrical stimulation to one or more muscle sites of patient 12 to inhibit patient movement in the fashion described in this disclosure. Electrical stimulation may be delivered to patient 12 via one or more electrodes implanted or located external to patient 12 via one or more implanted or external medical devices.

Moreover, in addition or instead of delivering of electrical stimulation to patient 12 to inhibit patient movement or otherwise treat RBD or symptoms thereof, in response to determining patient 12 is in an REM sleep state, IMD 16 or other medical device may deliver drug therapy to patient 12. For example, IMD 16 may be an implantable drug infusion device capable of delivering one or more therapeutic agents to patient 12. In some examples, for therapeutic agents requiring a relatively long period of time between the delivery and the time patient 12 experiences therapeutic effects from the therapeutic agents, IMD 16 may deliver the therapeutic agent in advance of patient 12 occupying a REM sleep stage so that patient 12 experiences the desired therapeutic effects in conjunction with occupying a REM sleep stage.

In the example shown in FIG. 1, IMD 16 may be implanted within a chest cavity of patient 12 or within a subcutaneous pocket below the clavicle over the chest cavity of patient 12. In other examples, IMD 16 may be implanted within other regions of patient 12, such as a subcutaneous pocket in the abdomen of patient 14 or proximate the cranium of patient 12. Implanted lead extension 18 is mechanically and electrically connected to IMD 16 via connector block 24, which may include, for example, electrical contacts that electrically couple to respective electrical contacts on lead extension 18. The electrical contacts electrically couple the electrodes 22A and 22B (collectively "electrodes 22") on lead 20 to IMD 16. Lead extension 18 traverses from the implant site of IMD 16 within patient 14, along the neck of patient 14 and through the cranium of patient 14 to access brain 12.

Although lead 20 is shown in FIG. 1 as a single lead, in other examples lead 20 may include multiple leads implanted within brain 13 of patient 12 to treat one or more disorders of patient 12. Lead 20 may be implanted within the right and/or left hemisphere of brain 12 in order to deliver electrical stimulation to one or more regions of brain 12, which may be selected based on many factors, such as the type of patient condition for which therapy system 10 is implemented to manage. In addition, in some examples, electrodes 22 on lead 20 may be used to sense brain activity. Different neurological or psychiatric disorders may be associated with activity in one or more of regions of brain 12, which may differ between patients.

Although lead 20 is shown in FIG. 1 as being coupled to lead extension 18, in other examples, lead 20 may be directly coupled to IMD 16. Lead 20 may deliver electrical stimulation to treat any number of psychiatric or neurological disorders or diseases in addition to treating RBD. For example, IMD 16 may deliver electrical stimulation therapy via electrodes 22 on lead 20 to brain 13 of a patient 12 to treat a movement disorder such as tremor, Parkinson's disease (PD), multiple sclerosis, or spasticity. Examples of psychiatric disorders that may be treated by delivery of electrical stimulation from IMD 16 to brain 13 of patient 12 may include major depressive disorder, anxiety, hypomania or bipolar disorder.

In addition to electrical stimulation therapy, a suitable pharmaceutical agent, such as acetylcholine, dopamine, epinephrine, norepinephrine, serotonine, inhibitors of noradrenaline or any agent for affecting a sleep disorder or combinations thereof may be delivered to patient 12 (e.g., delivered to brain 13 or another region within patient 12). An example drug delivery system is described below with regard to FIGS. 6 and 7. By alleviating the patient's sleep disturbances and improving the quality of the patient's sleep, patient 12 may feel more rested, and, as a result, DBS system 10 may help improve the quality of the patient's life. In some examples, one or more therapeutic agents used to treat restless leg syndrome (RLS) may be used to treat one or more symptoms of RBD.

Lead 20 may be implanted within a desired location of brain 13 via any suitable technique, such as through a burr hole in a skull of patient 12. Lead 20 may be placed at any location within brain 13 such that the electrodes of the leads are capable of providing electrical stimulation to targeted tissue during treatment. Electrical stimulation generated from the stimulation generator (not shown) of the therapy module of IMD 16 and delivered to brain 13 of patient 12 may help prevent the onset of symptoms or mitigate the symptoms associated with the patient's neurological disorder being treated by DBS system 10. For example, in the case of IMD 16 delivering electrical stimulation therapy to patient 12 to treat RBD, the electrical stimulation generated and delivered to patient 12 may reduce or prevent uncontrolled movement of patient 12 associated with RBD while patient 12 is in a REM sleep stage.

In some examples, lead 20 may be implanted such that electrodes 22B (or some electrodes positioned distally on lead 20) are capable of delivering electrical stimulation to the PPN or other midbrain nuclei, while electrode 22A (or other electrodes positioned more proximally on lead 20) are capable of delivering electrical stimulation to the GPi and/or other basal ganglia such as the STN. In this manner, IMD 16 may deliver stimulation to multiple tissue sites via a single lead. Each target tissue site may be used from stimulation to treat RBD. In some examples, one or both of the target tissue sites may be used to treat other patient disorders, such as, e.g., Parkinson's disease. As RBD may be exhibited in advance of PD, the implantation of lead 20 as described may allow electrical stimulation to be delivered to initially treat RBD, with the option of additionally treating PD (e.g., via STN stimulation) at some later point in time without having to reposition lead 20 within brain 13 or implant another lead to target one or more tissues sites used to treat PD.

The exact stimulation therapy parameter values of the stimulation therapy, such as the amplitude or magnitude of the stimulation signals, the duration of each signal, the waveform of the stimuli (e.g., rectangular, sinusoidal or ramped signals), the frequency of the signals, and the like, may be specific for the particular target stimulation site (e.g., the region of the brain) involved as well as the particular patient and patient condition.

In the case of stimulation pulses, the stimulation therapy may be characterized by selected pulse parameters, such as pulse amplitude (voltage or current), pulse rate, and pulse width. In addition, if different electrodes are available for delivery of stimulation, the therapy may be further characterized by different electrode combinations. Known techniques for determining the desirable stimulation parameters may be employed. Stimulation parameters may be selected such to treat one or more symptoms of a patient disorder. For example, in the case of RBD, stimulation parameters (in combination with the target tissue site(s)) may be selected to inhibit movement of patient 12 while in a REM sleep stage. In this manner, uncontrolled physical movement of patient 12 during REM sleep associated with RBD may be reduced or prevent by the delivery of electrical stimulation from IMD 16 to brain 13 of patient 12.

Electrodes 22 may be arranged in unipolar, bipolar, or multipolar combinations for delivery of stimulation. A unipolar stimulation arrangement generally refers to the use of an anode on the housing of IMD 16 that sources current and one or more cathodes on one or more leads that sink current. A bipolar stimulation arrangement generally refers to the use of an anode on a lead that sources current and a cathode on the same lead and/or another lead that sink current. A multipolar stimulation arrangement generally refers to the use of more than one anode on a lead that each source current and one or more cathodes on the same lead or another lead that sink current, or the use of one anode on a lead that sources current and multiple cathodes on the same lead or another lead that sink current Electrodes 22 of lead 20 are shown as ring electrodes. Ring electrodes may be relatively easy to program and are typically capable of delivering an electrical field to any tissue adjacent to lead 20. In other examples, electrodes 22 of lead 20 may have different configurations. For example, electrodes 22 of leads 20 may have a complex electrode array geometry that is capable of producing electrical fields having predefined shapes, e.g., that are selected based on the target tissue sites within brain 13 for the electrical stimulation. The complex electrode array geometry may include multiple electrodes (e.g., partial ring or segmented electrodes) around the perimeter of lead 20, rather than a ring electrode. In this manner, electrical stimulation may be directed to a specific direction from lead 20 to enhance therapy efficacy and reduce possible adverse side effects from stimulating a large volume of tissue. In some examples, a housing of IMD 16 may include one or more stimulation and/or sensing electrodes. In alternative examples, lead 20 may have a shape other than the elongated cylinder as shown in FIG. 1. For example, lead 20 may be a paddle lead, spherical lead, bendable lead, or any other type of shape effective in treating patient 12.

In some examples, one or more of electrodes 22 on lead 20 may be used to sense electrical signals within one or more region of patient's brain 12. Alternatively, another set of sensing electrodes other than that used to deliver electrical stimulation to brain 13 of patient 12 may monitor the electrical signals in brain 13. In general, the electrical signals within the patient's brain 13 may be interchangeably referred to herein as biosignals or bioelectrical brain signals. The biosignal may include a bioelectrical signal, such as an electroencephalogram (EEG) signal, an electrocorticogram (ECoG) signal, a local field potential (LFP) sensed from within one or more regions of patient's brain 13, and/or action potentials from single cells within the patient's brain. For example, a sensed brain signal may include an EEG signal, which may be generated via one or more electrodes implanted and/or located external to patient 12. Electrodes implanted closer to the target region of brain 13 may help generate an electrical signal that provides more useful information than an EEG generated via a surface electrode array because of the proximity to brain 13. The EEG signal that is generated from an electrode array implanted within brain 13 may also be referred to as an electrocorticography (ECoG) signal.

As will be described further below, IMD 16 may generate deliver electrical stimulation therapy to treat RBD of patient 12. For example, IMD 16 may generate and deliver electrical stimulation therapy to brain 13 of patient 12 upon determining patient 12 is in a REM sleep stage. The therapy delivered by IMD 16 to brain 13 via one or more of electrodes 22 may treat RBD of patient 12 by reducing or preventing uncontrolled physical movements of patient 12 during a REM sleep stage that are attendant to RBD. In some examples, to determine when to deliver electrical stimulation therapy, IMD 16 may monitor biosignals of brain 13, e.g., via one or more sense electrodes implanted and/or located external to brain 13 of patient 12. When the biosignals of patient 12 sensed by IMD 16 are indicative of patient 12 being in a REM sleep stage, IMD 16 may generate and deliver electrical stimulation therapy to one or more tissue sites in brain 13 to inhibit undesired physical movement of patient 12 associated with RBD. In some examples, the biosignals with which a REM sleep stage of patient 12 is determined are detected within the same tissue site of brain 13 as the target tissue site for delivery of electrical stimulation. In other examples, the biosignals may be detected within another tissue site. IMD 16 may deliver such therapy to brain 13 of patient 12 during all or a portion of the time period patient 12 is in a REM sleep stage. In this manner, IMD 16 may deliver therapy to patient 12 to combat undesirable symptoms of RBD experienced by patient 12 when in a REM sleep stage.

IMD 16 may be constructed of a biocompatible material that resists corrosion and degradation from bodily fluids. IMD 16 may comprise a hermetic housing or a near hermetic housing to substantially enclose components, such as a processor, therapy module, and memory. IMD 16 may be implanted within a subcutaneous pocket close to the stimulation site. As previously described, although IMD 16 is implanted within a subcutaneous pocket above the clavicle of patient 12 in the example shown in FIG. 1, in other examples, IMD 16 may be implanted on or within cranium 26, within the patient's back, abdomen, or any other suitable place within patient 12.

Programmer 14 is an external computing device that the user, e.g., the clinician and/or patient 12, may use to communicate with IMD 16. For example, programmer 14 may be a clinician programmer that the clinician uses to communicate with IMD 16 and program one or more therapy programs for IMD 16. Alternatively, programmer 14 may be a patient programmer that allows patient 12 to select programs and/or view and modify electrical stimulation parameters. The clinician programmer may include more programming features than the patient programmer. In other words, more complex or sensitive tasks may only be allowed by the clinician programmer to prevent an untrained patient from making undesired changes to IMD 16.

Programmer 14 may be a hand-held computing device with a display viewable by the user and an interface for providing input to programmer 14 (i.e., a user input mechanism). For example, programmer 14 may include a small display screen (e.g., a liquid crystal display (LCD) or a light emitting diode (LED) display) that provides information to the user. In addition, programmer 14 may include a touch screen display, keypad, buttons, a peripheral pointing device or another input mechanism that allows the user to navigate though the user interface of programmer 14 and provide input. If programmer 14 includes buttons and a keypad, the buttons may be dedicated to performing a certain function, i.e., a power button, or the buttons and the keypad may be soft keys that change in function depending upon the section of the user interface currently viewed by the user. Alternatively, the screen (not shown) of programmer 14 may be a touch screen that allows the user to provide input directly to the user interface shown on the display. The user may use a stylus or a finger to provide input to the display.

In other examples, programmer 14 may be a larger workstation or a separate application within another multi-function device, rather than a dedicated computing device. For example, the multi-function device may be a notebook computer, tablet computer, workstation, cellular phone, personal digital assistant or another computing device may run an application that enables the computing device to operate as medical device programmer 14. A wireless adapter coupled to the computing device may enable secure communication between the computing device and IMD 16.

When programmer 14 is configured for use by the clinician, programmer 14 may be used to transmit initial programming information to IMD 16. This initial information may include hardware information, such as the type of lead 20 and the electrode 22 arrangement, the position of lead 20 within brain 13, the configuration of electrode array 22, initial programs defining electrical stimulation parameter values, and any other information the clinician desires to program into IMD 16. Programmer 14 may also be capable of completing functional tests (e.g., measuring the impedance of electrodes 22).

Programmer 14 may be used by a clinician to control delivery of electrical stimulation, such as by activating electrical stimulation, deactivating electrical stimulation, or adjusting one or more stimulation parameters of therapy being delivered to patient 12. The clinician may also store therapy programs within IMD 16 with the aid of programmer 14. During a programming session, the clinician may determine one or more therapy programs that may provide efficacious therapy to patient 12 to address symptoms associated a disorder of patient 12 such as RBD. Patient 12 may provide feedback to the clinician as to the efficacy of the specific program being evaluated.

Programmer 14 may also be configured for use by patient 12. When configured as a patient programmer, programmer 14 may have limited functionality (compared to a clinician programmer) in order to prevent patient 12 from altering critical functions of IMD 16 or applications that may be detrimental to patient 12. In this manner, programmer 14 may only allow patient 12 to adjust values for certain electrical stimulation parameters or set an available range of values for a particular electrical stimulation parameter.

Programmer 14 may also provide an indication to patient 12 when therapy is being delivered, when patient input has triggered a change in electrical stimulation parameters or when the power source within programmer 14 or IMD 16 needs to be replaced or recharged. For example, programmer 14 may include an alert LED, may flash a message to patient 12 via a programmer display, or may generate an audible sound or somatosensory cue to confirm patient input was received, e.g., to indicate a patient state or to manually modify an electrical stimulation parameter.

Whether programmer 14 is configured for clinician or patient use, programmer 14 is configured to communicate to IMD 16 and, optionally, another computing device, via wireless communication. Programmer 14, for example, may communicate via wireless communication with IMD 16 using radio frequency (RF) telemetry techniques known in the art. Programmer 14 may also communicate with another programmer or computing device via a wired or wireless connection using any of a variety of local wireless communication techniques, such as RF communication according to the 802.11 or Bluetooth™ specification sets, infrared (IR) communication according to the IRDA specification set, or other standard or proprietary telemetry protocols. Programmer 14 may also communicate with other programming or computing devices via exchange of removable media, such as magnetic or optical disks, memory cards or memory sticks. Further, programmer 14 may communicate with IMD 16 and another programmer via remote telemetry techniques known in the art, communicating via a local area network (LAN), wide area network (WAN), public switched telephone network (PSTN), or cellular telephone network, for example.

DBS system 10 may be implemented to provide chronic stimulation therapy to patient 12 over the course of several months or years. However, DBS system 10 may also be employed on a trial basis to evaluate therapy before committing to full implantation. If implemented temporarily, some components of system 10 may not be implanted within patient 12. For example, patient 12 may be fitted with an external medical device, such as a trial stimulator, rather than IMD 16. The external medical device may be coupled to percutaneous leads or to implanted leads via a percutaneous extension. If the trial stimulator indicates DBS system 10 provides effective treatment to patient 12, the clinician may implant a chronic stimulator within patient 12 for relatively long-term treatment.

Figure 6:
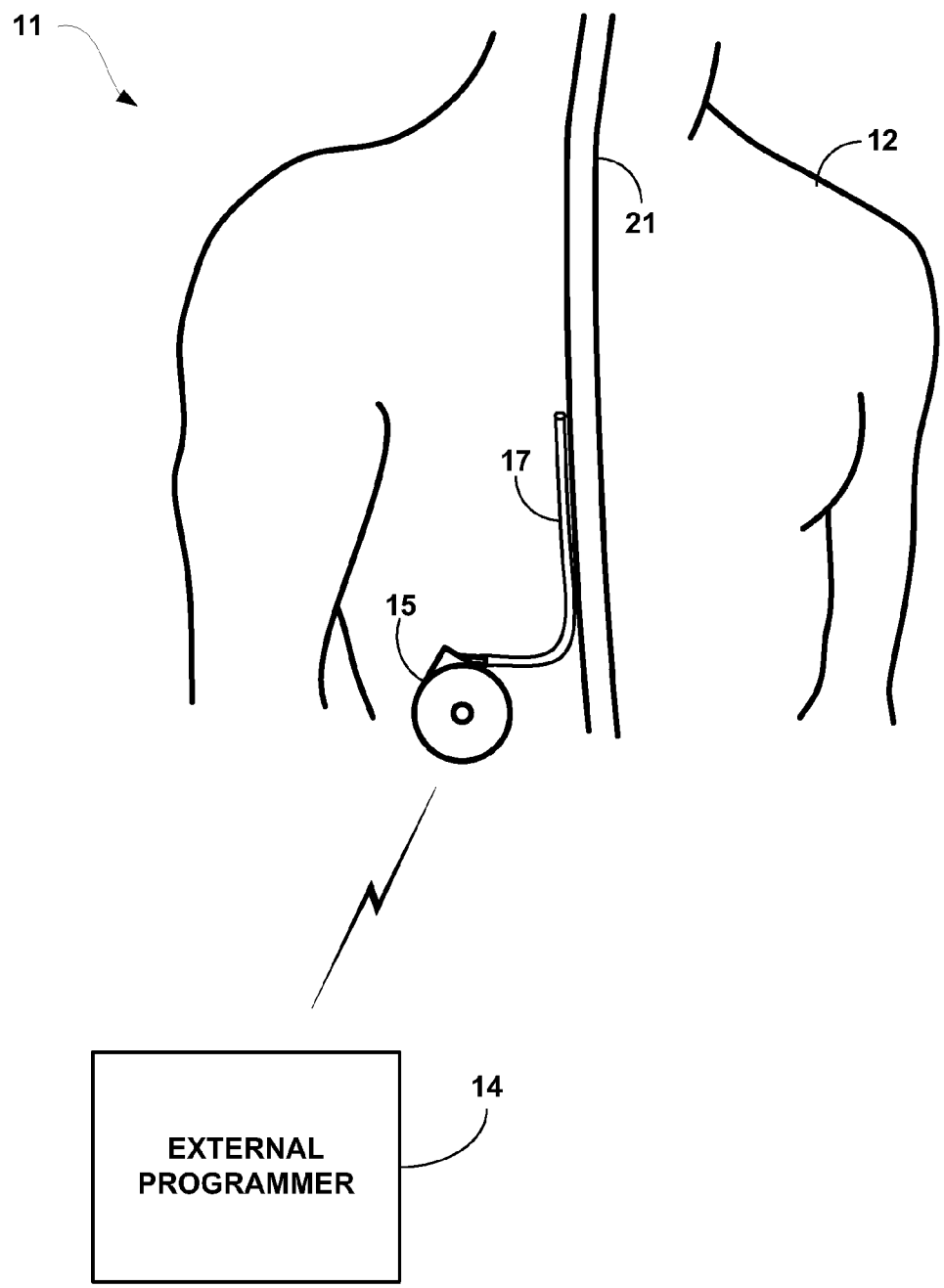
FIG. 6 is a conceptual diagram illustrating an example implantable drug delivery system.

FIG. 6 is a conceptual diagram illustrating an implantable drug delivery system 11 including one delivery catheter 17 coupled to IMD 15. Drug delivery system 11 may be substantially similar to system 10 in one or more aspects. However, drug delivery system 11 performs the similar therapy functions via delivery of one or more therapeutic agents instead of electrical stimulation therapy. IMD 15 functions as a drug pump in the example of FIG. 6, and IMD 15 communicates with external programmer 14 to initialize therapy or modify therapy during operation. In addition, IMD 15 may be refillable to allow chronic drug delivery.

As shown in the example of FIG. 6, fluid delivery port of catheter 17 may be positioned within an intrathecal space or epidural space of spinal cord 21. Although IMD 15 is shown as coupled to only one catheter 17 positioned along spinal cord 21, additional catheters may also be coupled to IMD 15. Multiple catheters may deliver drugs or other therapeutic agents to the same anatomical location or the same tissue or organ. Alternatively, each catheter may deliver therapy to different tissues within patient 12 for the purpose of treating multiple symptoms or conditions. As described above, in some examples, IMD 15 may deliver one or more drugs or other therapeutic agents to treat RBD, e.g., by inhibiting (reducing or eliminating) the physical movement of patient 12 that is symptomatic of RBD during REM sleep. In some examples, IMD 15 may be an external device that includes a percutaneous catheter to deliver a therapeutic agent to patient 12, e.g., in the same manner as catheter 17. Alternatively, the percutaneous catheter can be coupled to catheter 17, e.g., via a fluid coupler. In other examples, IMD 15 may include both electrical stimulation capabilities as described in IMD 16 (FIG. 1) and drug delivery therapy.

IMD 17 may also operate using parameters that define the method of drug delivery. IMD 17 may include programs, or groups of programs, that define different delivery methods for patient 12. For example, a program that controls delivery of a drug or other therapeutic agent may include a titration rate or information controlling the timing of bolus deliveries. Patient 12 may use external programmer 14 to adjust the programs or groups of programs to regulate the therapy delivery.

Figure 2:
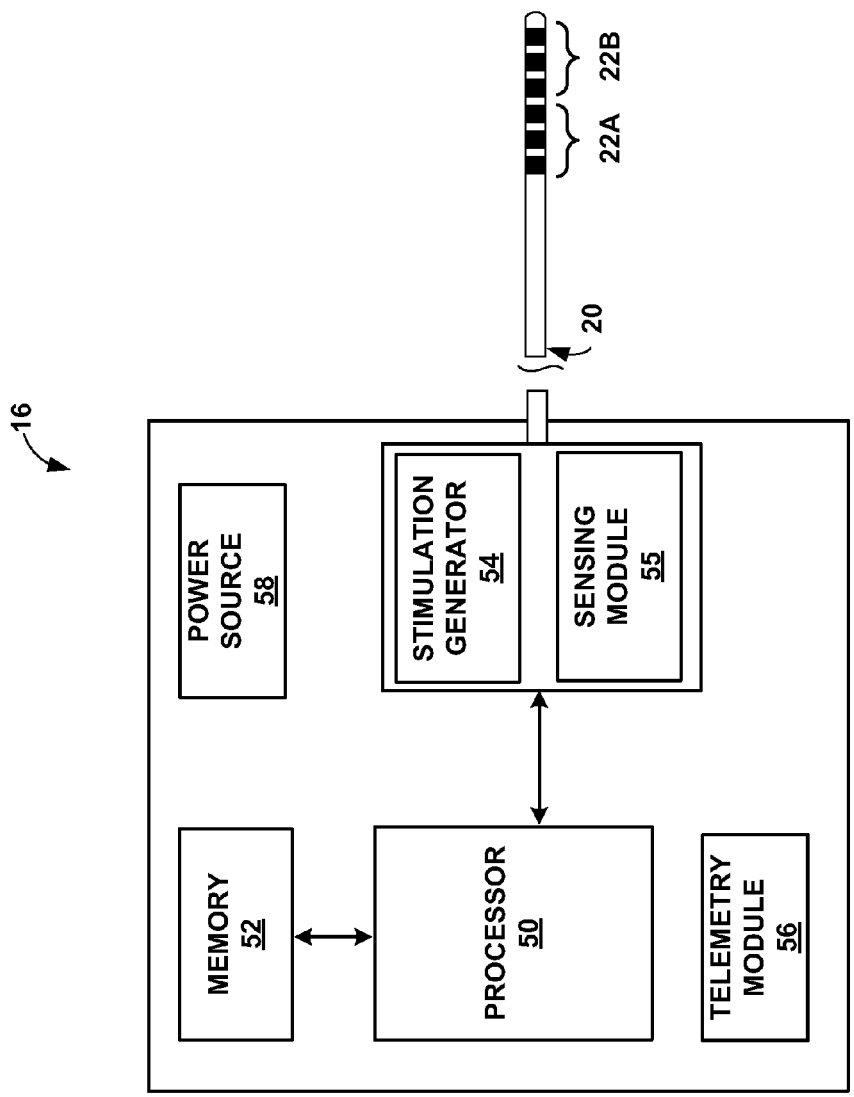
FIG. 2 is a functional block diagram illustrating components of an example medical device.

FIG. 2 is a functional block diagram illustrating components of an example IMD 16. In the example shown in FIG. 2, IMD 16 generates and delivers electrical stimulation therapy to patient 12. IMD 16 includes processor 50, memory 52, stimulation generator 54, sensing module 55, telemetry module 56, and power source 58. Although sensing module 55 is shown to be a component of IMD 16 in FIG. 2, in other examples, sensing module 55 and IMD 16 may be separate devices and may be electrically coupled, e.g., via a wired or wireless connection.

Memory 52 may include any volatile or non-volatile media, such as a random access memory (RAM), read only memory (ROM), non-volatile RAM (NVRAM), electrically erasable programmable ROM (EEPROM), flash memory, and the like. Memory 52 may store instructions for execution by processor 50 and information defining delivery of electrical stimulation to patient 12, such as, but not limited to, therapy programs (e.g., sets of stimulation parameter values) or therapy program groups, information associating therapy programs with one or more sleep stages, thresholds or other information used to detect a REM sleep stage based on sensed biosignals, and any other information regarding therapy of patient 12. Therapy information may be recorded in memory 52 for long-term storage and retrieval by a user. Memory 52 may include separate memories for storing information, such as separate memories for therapy programs, REM sleep stage information, diagnostic information, target tissue site information, and patient information. In some examples, memory 52 stores program instructions that, when executed by processor 50, cause IMD 16 and processor 50 to perform the functions attributed to them herein.

Memory 52 may be considered, in some examples, a non-transitory computer-readable storage medium comprising instructions that cause one or more processors, such as, e.g., processor 50, to implement one or more of the example techniques described in this disclosure. The term "non-transitory" may indicate that the storage medium is not embodied in a carrier wave or a propagated signal. However, the term "non-transitory" should not be interpreted to mean that memory 52 is non-movable. As one example, memory 52 may be removed from IMD 16, and moved to another device. In certain examples, a non-transitory storage medium may store data that can, over time, change (e.g., in RAM).

Processor 50 controls stimulation generator 54 to deliver electrical stimulation therapy to brain 13 of patient 12 via lead 20. As described above, processor 50 may control stimulation generator 54 to generate and deliver electrical stimulation to one or more tissue sites of brain 13 when patient 12 is determined to be in a REM sleep stage. Processor 50 may control the delivery of such stimulation to brain 13 of patient 12 in a manner that inhibits patient movement associated with RBD while patient 12 is in a REM sleep stage.

In some examples, IMD 16 may deliver electrical stimulation therapy to one or more of the GPi, STN, and other basal ganglia of patient 12 to treat RBD when patient 12 is determined to occupy a REM sleep stage. In some examples, delivery of electrical stimulation to such exemplary tissue sites may cause rigidity in patient 12. An example range of electrical stimulation parameters believed to be effective in DBS delivered to such tissue sites of brain 13 (FIG. 1) to manage symptoms associated with RDB when patient 12 is in a REM sleep stage are:

1. Frequency: between approximately 8 and approximately 30 Hz, such as, e.g., between approximately 13 Hz and 25 Hz.

2. Amplitude: between approximately 0.1 volts and approximately 50 volts, such as, e.g., between approximately 2 volts and approximately 6 volts. In other examples, rather than a voltage controlled system, the stimulation system may control the current. A current amplitude may be defined as the biological load in the voltage that is delivered. The range of current amplitude may be between approximately 0.01 milliamps (mA) and approximately 50 mA, such as, e.g., between approximately 0.1 milliamps (mA) and approximately 10 mA.

3. Pulse Width: between approximately 20 microseconds and approximately 450 microseconds, such as, e.g., between approximately 60 microseconds and approximately 100 microseconds.

In some examples, IMD 16 may deliver electrical stimulation therapy to one or more midbrain tissue sites of patient 12 to treat RBD when patient 12 is determined to occupy a REM sleep stage. Suitable midbrain tissue sites for delivery of electrical stimulation may include midbrain nuclei, such as, e.g., the RRN, vFTP, TRN, and PPN nuclei. In some examples, delivery of electrical stimulation to such exemplary tissue sites may cause relaxation of patient muscle tone to inhibit undesired movement of patient 12 associated with RBD when patient 12 is in a REM sleep stage. An example range of electrical stimulation parameters believed to be effective in DBS delivered to such tissue sites of brain 13

(FIG. 1) to manage symptoms associated with RDB when patient 12 is in a REM sleep stage include:

1. Frequency: between approximately 50 and approximately 200 Hz, such as, e.g., between approximately 100 Hz and 185 Hz.

2. Amplitude: between approximately 0.1 volts and approximately 50 volts, such as, e.g., between approximately 2 volts and approximately 10 volts. In other examples, rather than a voltage controlled system, the stimulation system may control the current. A current amplitude may be defined as the biological load in the voltage that is delivered. The range of current amplitude may be between approximately 0.01 milliamps (mA) and approximately 10 mA, such as, e.g., between approximately 0.02 milliamps (mA) and approximately 10 mA.

3. Pulse Width: between approximately 20 microseconds and approximately 450 microseconds, such as, e.g., between approximately 60 microseconds and approximately 100 microseconds.

IMD 16 may deliver stimulation to tissue sites other than those example tissue sites listed above. Other ranges of therapy parameter values may also be useful, and may depend on the target stimulation site within patient 12. One or more details of the examples of electrical stimulation sites that may be utilized as target sites for electrical stimulation may include one or more of those described in the document titled "Muscle Tone Suppression and Stepping Produced by Stimulation of Midbrain and Rostral Pontine Recticular Formation" by Lai et al., Journal of Neuroscience, vol. 10, p. 2727-2734, August 1990. In some examples, example target sites may include midbrain retrorubral (RRN), ventral paralemniscal tegmental field (vFTP), reticular tegmental (TRN), and/or pedunculopontine tegmental (PPN) nuclei. In some examples, example target site may include basal ganglia (BG) (which include a group of interconnected subcortical nuclei), the pedunculo-pontine nucleus (PPN) (which may be highly and reciprocally interconnected with the BG), the subthalamic nucleus (STN) (which may send glutamatergic projection to the PPN which, in turn, may send cholinergic, glutamatergic and GABAergic projections back to the STN), the globus pallidus pars interna (GPi), the substantia nigra pars reticulata (SNr). The delivered stimulation may be unipolar or multi-polar bi-polar) and may be unilateral or bilateral. Other stimulation sites are contemplated.

While stimulation pulses are described, stimulation signals may be of any form, such as continuous-time signals (e.g., sine waves) or the like. The physiological effects of the delivered electrical stimulation therapy are not limited to those described above. For example, in some instance, processor 50 may control the delivery of therapy to brain 13 to cause akinesia, atonia, or other condition in patient 12 to reduce or prevent physical movement associated with RBD while patient 12 is in a REM sleep stage. In each case, the electrical stimulation therapy delivered to brain 13 of patient 12 may be effective in treating symptoms associated with RBD when patient 12 is in a REM sleep stage. As described above, in some examples, processor 50 can control stimulation generator 54 to generate stimulation that is delivered to multiple tissue sites of brain 13 of patient 12 according to the stimulation parameters of different therapy programs.

Processor 50 may also control delivery of electrical stimulation to patient 12 by delivering electrical stimulation to one target tissue site with particular electrodes (e.g., electrodes 22A of DBS system 10) and to another target tissue site with different electrodes (e.g., electrodes 22B of DBS system 10). For example, in one instance, electrical stimulation may be delivered to the subthalamic nucleus (or other basal ganglia) of brain 13 of patient 12 via electrodes 22A and to the PPN (or other midbrain nuclei) of brain 13 of patient 12 via electrodes 22B. In some cases, electrical stimulation may be delivered via electrodes 22A according to a particular therapy program and via electrodes 22B according to a different therapy program. Electrical stimulation via electrodes 22A and 22B may be controlled independently, and may be controlled and delivered either simultaneously or alternatively. In other examples, processor 50 may control delivery of electrical stimulation by delivering electrical stimulation to several different target tissue sites with some or all of the same electrodes.

Processor 50 may include any one or more of a microprocessor, a controller, a digital signal processor (DSP), an application specific integrated circuit (ASIC), a field-programmable gate array (FPGA), discrete logic circuitry, and the functions attributed to processor 50 herein may be embodied as firmware, hardware, software or any combination thereof. In general, components described as processors within IMD 12, external programmer 14 or any other device described in this disclosure may each comprise one or more processors, such as one or more microprocessors, DSPs, ASICs, FPGAs, programmable logic circuitry, or the like, either alone or in any suitable combination. The functions attributed to processors described herein may be provided by a hardware device and embodied as software, firmware, hardware, or any combination thereof.

Processor 50 may determine whether or not patient 12 is in a REM sleep stage based on one or more biosignals sensed via sensing module 55. In some examples, sensing module 55 may generate a signal indicative of electrical activity within brain 13 of patient 12 using one or more of electrodes 22 as sense electrodes, as shown in FIG. 2. In this way, sensing module 55 may detect or sense a biosignal within brain 13 of patient 12. Although sensing module 55 is incorporated into a common housing with stimulation generator 54 and processor 50 in FIG. 2, in other examples, sensing module 55 may be in a separate housing from IMD 16 and may communicate with processor 50 via wired or wireless communication techniques. Sensing module 55 may use the same or different electrode to sense one or more biosignals of brain 12 as that used to delivery electrical stimulation generated by stimulation generator 54 to patient 12.

Sensing module 55 is configured to generate an electrical signal indicative of activity within brain 13 of patient and/or other physiological parameters of patient 12. As previously indicated, example electrical signals that sensing module 55 may sense include, but are not limited to, a signal generated from local field potentials within one or more regions of brain 13. EEG and ECoG signals are examples of local field potentials that may be measured within brain 13. However, local field potentials may include a broader genus of electrical signals within brain 13 of patient 12.

To determine when patient 12 is in a REM sleep stage, sensing module 55 may detect or sense a biosignal within brain 13 of patient 12 and the sensed information may be transmitted to processor 50 for analysis. In some examples, processor 50 accesses memory 52 to retrieve one or more previously recorded biosignals that are stored in memory 52. Processor 50 may compare the detected biosignal to one or more previously recorded biosignal indicative of a REM sleep stage of patient in order to determine whether patient 12 is in a REM sleep stage. For example, processor 50 may compare a particular characteristic of the detected biosignal to the same characteristic (e.g., a signature biosignal characteristic) of the previously recorded biosignals indicative of patient 12 occupying a REM sleep stage to determine whether the characteristics are the same. Example signal characteristics that can be compared include, but are not limited to, a power level within one or more frequency bands, a ratio of power levels within two or more frequency bands, a peak, average or lowest biosignal amplitude within a particular range of time, a characteristic waveform of the biosignal (e.g. "saw-tooth" wave forms from an EEG signal, Ponto-geniculo-occipital (PGO) waves, rapid eye movement), a pattern in a biosignal amplitude over time, and the like. In some examples, characteristics of other sleep stages, such as, e.g., EEG sleep spindle activity indicative of sleep stage 2, may be used to determine that patient 12 is not in a REM sleep stage.

If the signal characteristics between the sensed biosignal and the stored biosignal substantially match (e.g., are within a threshold range, which may be, for example about 75% to about 100%), processor 50 may determine that patient 12 is in a REM sleep stage. If processor 50 determines that the detected biosignal does not substantially match the previously recorded biosignal characteristic, processor 50 may determine that patient 12 is not in a REM sleep stage.

Alternatively or additionally, processor 50 may compare sensed biosignals to previously recorded biosignals that are indicative of patient 12 not being in REM sleep stage. For example, such biosignals may be indicative of patient 12 not sleeping but being awake or may be indicative of patient 12 being asleep but in a sleep stage different than that of a REM sleep stage. In such a case, processor 50 may determine that patient 12 is not in a REM sleep stage if the sensed biosignals substantially match previously recorded biosignals, but may determine that patient 12 is in a REM sleep stage if the sensed biosignals do not substantially match any of the previously recorded biosignals.

In addition to or instead of comparing the characteristic of the biosignal to a stored signal reflecting a previously recorded biosignal of patient 12, processor 50 may compare a characteristic of a biosignal sensed via a specific subset of electrodes 22 to a template or threshold stored in memory 52 that is indicative of patient 12 being in a REM sleep stage. The threshold values may be, for example, threshold power levels within selected frequency bands that indicate a particular sleep stage, or values that are generated based on ratios of power between two or more frequency bands. A template may be, for example, a waveform template or a pattern in power levels of the biosignal within a selected frequency band over time. The template or threshold stored by memory 52 can be generally applicable or specific to one or more sensing locations. The thresholds may be patient specific or may be generally applicable to more than one patient. Processor 50 may access such biosignal information to determine, based on the threshold values or templates, whether a detected biosignal is indicative of patient 12 being in a REM sleep stage. Alternatively or additionally, processor 50 may determine patient 12 occupies a REM sleep stage based on body temperature, muscle tone (e.g., sensed via EMG), eye movement, actigraphy in combination with EMG signals, or some combination thereof.

In addition to or instead of monitoring biosignals of patient 12 via electrodes 22 coupled to lead 20, processor 50 may directly or indirectly receive biosignals indicative of electrical activity within brain 13 from electrodes coupled to another lead that is electrically coupled to sensing module 55, biosignals from electrodes coupled to an outer housing of IMD 16 and electrically coupled to sensing module 55, and/or biosignals from a sensing module that is separate from IMD 16.

In some examples, processor 50 may monitor and detect the physical movement of patient 12 via sensing module 55. For example, in some cases, sensing module 55 may include or be coupled to one or more accelerometer sensors capable of detection patient movement and/or posture. Such accelerometer sensors may be contained in IMD 16 and/or may be located remotely at one or more locations within or on patient 12. Processor 50 may analyze the accelerometer sensor signals to detect physical movement of patient 12. Additionally or alternatively, sensing module 55 may be configured to generate an EMG signal to allow processor 50 to monitor the muscle tone of patient 12. In each case, processor 50 may detect the physical movement of patient 12 via sensing module 55. As will be described below, processor 50 may use the physical movement of patient 12 as a trigger for the delivery of electrical stimulation to patient 12 to treat RBD and/or as an indicator as to the effectiveness of therapy being delivered to patient 12 inhibiting the physical movement of patient 12 while in a REM sleep stage.

In some examples, processor 50 may monitor both the physical movement of patient 12 and instances of patient 12 being in a REM sleep stage, and store such information in memory 52. This information may then be presented to a user, e.g., via programmer 14, for review and/or analyzed by processor 50. For example, based on the substantially simultaneous monitoring of physical movement of patient 12 and instance of patient 12 occupying a REM sleep stage, a user may quantify one or more aspects of episodes of RBD experience by patient 12. Additionally, the efficacy of therapy that is delivered to patient 12 to treat RBD may be gauged using such information. For example, movement of patient 12 during a REM sleep stage while therapy is being delivered to patient 12 may be compared to the movement of patient 12 during a REM sleep stage when therapy is not being delivered. In some examples, therapy modifications may be implemented and/or reviewed using such information.

As will be described below, processor 50 may control delivery of electrical stimulation generated by stimulation generator 54 to deliver electrical stimulation to brain 13 of patient 12 to treat one or more symptoms of RBD when processor 50 determines that patient 12 is in a REM sleep stage, e.g., based on sensed biosignals. For instances in which electrical stimulation therapy is being delivered to brain 13 of patient 12 by IMD 12 when patient 12 is determined to be in a REM sleep stage, e.g., to treat one or more other movement or sleep disorders, processor 50 may modify the electrical stimulation to treat the symptoms of RBD, in addition to or as an alternative to, the other disorders being treated by IMD 16. In some examples, IMD 16 delivers baseline electrical stimulation in order to maintain a particular patient state, such as a baseline state in which the patient symptoms are manageable, when patient 12 is not in a REM sleep stage, but may modify the stimulation, e.g., by adjusting the tissue sites that electrical stimulation is delivered and/or adjusting one or more stimulation parameters of the therapy, to treat the symptoms of RBD experienced by patient 12 when processor 50 determines patient 12 is in a REM sleep stage.

In the example shown in FIG. 2, processor 50 may select one or more therapy programs from memory 52 to define the electrical stimulation delivered to patient 12 to treat symptoms of RBD when patient 12 is determined to be in a REM sleep stage. Alternatively, programmer 14 may store one or more therapy programs, and processor 50 of IMD 16 may receive selected programs from programmer 14 via telemetry circuit 56. For example, processor 70 of programmer 14 (FIG. 3) may select one or more therapy programs from memory 72 and transmit the selected therapy program(s) to processor 50, which may then control stimulation generator 54 to deliver therapy according to the selected therapy program(s).

As described above, in the case of electrical stimulation therapy, each of the programs stored in memory 52 (or memory 74 of programmer 14) may include respective values for a plurality of therapy parameters, such as voltage or current amplitude, signal duration, frequency, and electrode configuration (e.g., an indication of the electrodes 22 selected to deliver stimulation and the respective polarity of the electrodes). The therapy programs stored in memory 52 may be generated using programmer 14, e.g., during an initial or follow-up programming session, and received by processor 50 from programmer 14 via telemetry module 56. Multiple different therapy programs may be defined for treating RBD when patient 12 is determined to be in a REM sleep stage. In some examples, if processor 50 determines that therapy being delivered to patient 12 is not adequately treating RBD systems of patient 12 (e.g., when patient movement is detected during the delivery of such therapy to brain 13), processor 50 may terminate the delivery of therapy according to the therapy program and initiate delivery of electrical stimulation therapy to patient 12 according to a different therapy program defined to treat symptoms of RBD when patient is in a REM sleep stage.

Processor 50 controls telemetry module 56 to send and receive information. Telemetry module 56 in IMD 16, as well as telemetry modules in other devices and systems described herein, such as programmer 14, may accomplish communication by RF communication techniques. In addition, telemetry module 56 may communicate with external medical device programmer 14 via proximal inductive interaction of IMD 16 with programmer 14. Accordingly, telemetry module 56 may send information to external programmer 14 on a continuous basis, at periodic intervals, or upon request from IMD 16 or programmer 14.

Power source 58 delivers operating power to various components of IMD 16. Power source 58 may include a small rechargeable or non-rechargeable battery and a power generation circuit to produce the operating power. Recharging may be accomplished through proximal inductive interaction between an external charger and an inductive charging coil within IMD 16. In some examples, power requirements may be small enough to allow IMD 16 to utilize patient motion and implement a kinetic energy-scavenging device to trickle charge a rechargeable battery. In other examples, traditional batteries may be used for a limited period of time.

Memory 52 may store data relating to patient 12, such as the patient's name and age, the type of IMD 16 or leads 20 implanted within patient 12, medication prescribed to patient 12, and the like. Processor 50 of IMD 16 may also collect diagnostic information and store diagnostic information within memory 52 for future retrieval by a clinician. The diagnostic information may include other information or activities indicated by patient 12 using programmer 14, such as changes in symptoms, medication ingestion, or other activities of patient 12. A clinician may review diagnostic information 63 in a variety of forms, such as timing diagrams or a graph resulting from statistical analysis of diagnostic information 63, e.g., a bar graph. The clinician may, for example, download diagnostic information 63 from IMD 16 via programmer 14 or another computing device. Diagnostic information 63 may also include calibration routines for electrodes 22 (FIG. 1) and malfunction algorithms to identify stimulation dysfunctions.

Figure 7:
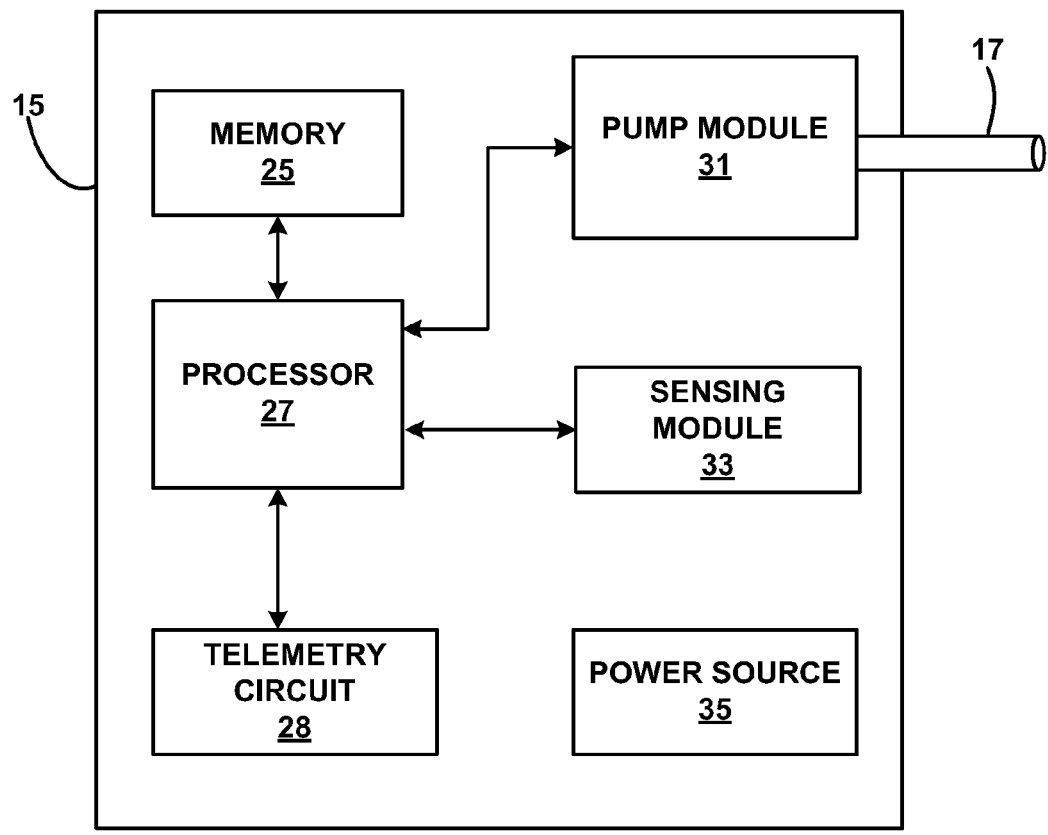
FIG. 7 is a functional block diagram illustrating various components of an example implantable drug delivery device.

FIG. 7 is a functional block diagram illustrating various components of an IMD 15, which delivers a therapeutic agent to patient 12. IMD 15 is a drug pump that operates substantially similar to IMD 14 of FIG. 2, but delivers a therapeutic agent instead of electrical stimulation. IMD 15 includes processor 27, memory 25, pump module 31, sensing module 33, telemetry circuit 28, and power source 35. Instead of stimulation generator 54 of IMD 14, IMD 15 includes pump module 31 for delivering drugs or some other therapeutic agent via catheter 17. Pump module 31 may include a reservoir to hold the drug and a pump mechanism to force the drug out of catheter 17 and into patient 12.

Processor 27 controls pump module 31 according to therapy instructions stored within memory 25. For example, memory 25 may contain the programs or groups of programs that define the drug delivery therapy for patient 12. A program may indicate the bolus size or flow rate of the drug, and processor 27 may accordingly deliver therapy. Processor 27 may also control pump module 31 to deliver drug therapy to patient 12 in a manner that treats RBD, e.g., by inhibiting (reducing or eliminating) the physical movement of patient 12 that is symptomatic of RBD during REM sleep.

Figure 3:
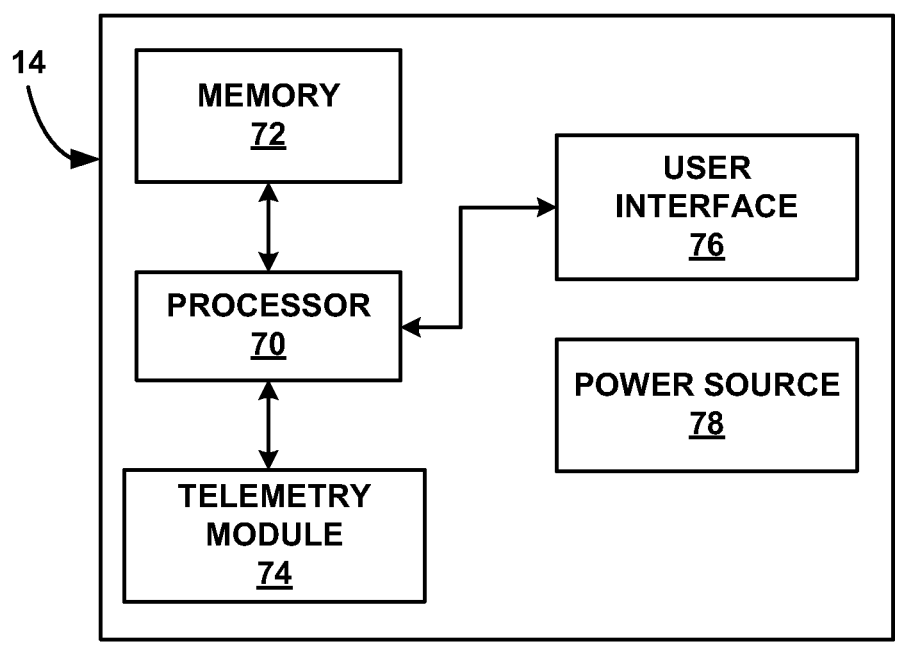
FIG. 3 is a functional block diagram illustrating components of an example medical device programmer.

FIG. 3 is a conceptual block diagram of an example external medical device programmer 14, which includes processor 70, memory 72, telemetry module 74, user interface 76, and power source 78. Processor 70 controls user interface 76 and telemetry module 74, and stores and retrieves information and instructions to and from memory 72. Programmer 14 may be configured for use as a clinician programmer or a patient programmer. Processor 70 may comprise any combination of one or more processors including one or more microprocessors, DSPs, ASICs, FPGAs, or other equivalent integrated or discrete logic circuitry. Accordingly, processor 70 may include any suitable structure, whether in hardware, software, firmware, or any combination thereof, to perform the functions ascribed herein to processor 70.

Processor 70 monitors activity from the input controls and controls the display of user interface 76. The user, such as a clinician or patient 12, may interact with programmer 14 through user interface 76. User interface 76 may include a display (not shown), such as an LCD or other type of screen, to present information related to the therapy, and input controls (not shown) to provide input to programmer 14. Input controls may include buttons, a keypad (e.g., an alphanumeric keypad), a peripheral pointing device, or another input mechanism that allows the user to navigate though the user interface of programmer 14 and to provide input. If programmer 14 includes buttons and a keypad, the buttons may be dedicated to performing a certain function, i.e., a power button, or the buttons and the keypad may be soft keys that change in function depending upon the section of the user interface currently viewed by the user. Alternatively, the screen (not shown) of programmer 14 may be a touch screen that allows the user to provide input directly to the user interface shown on the display. The user may use a stylus or their finger to provide input to the display. In other examples, user interface 76 also includes audio circuitry for providing audible instructions or sounds to patient 12 and/or receiving voice commands from patient 12, which may be useful if patient 12 has limited motor functions.

In some examples, at least some of the control of therapy delivery by IMD 16 may be implemented by processor 70 of programmer 14. For example, in some examples, processor 70 may receive a biosignal from IMD 16 or from a sensing module that is separate from IMD 16, where the biosignal is sensed within brain 13 by IMD 16 or the sensing module that is separate from IMD 16. The separate sensing module may, but need not be, implanted within patient 12. In some examples, processor 70 may determine whether or not patient 12 is in a REM sleep stage based on the detected biosignal and may transmit a signal to IMD 16 via telemetry module 74 indicating the determination. For example, processor 70 may determine whether or not patient 12 is in a REM sleep stage in a manner similar to that described above for processor 50 (FIG. 2) of IMD 16. Processor 50 of IMD 16 may receive the signal from programmer 14 via its respective telemetry module 56 (FIG. 3).

Processor 50 of IMD 16 may select one or more stored therapy programs from memory 52 based on the current sleep stage. Alternatively, processor 70 of programmer 14 may select a therapy program and transmit a signal to IMD 16, where the signal indicates the therapy parameter values to be implemented by IMD 16 during therapy delivery to treat symptoms of RBD when patient 12 is in a REM sleep stage, or may provide an indication of the selected therapy program that is stored within memory 52 of IMD 16. The indication may be, for example, an alphanumeric identifier or symbol that is associated with the therapy program in memory 52 of IMD 16.

Patient 12, a clinician or another user may also interact with programmer 14 to manually select therapy programs, generate new therapy programs, modify therapy programs through individual or global adjustments, and transmit the new programs to IMD 16. In a learning mode, programmer 14 may allow patient 12 and/or the clinician to determine which therapy programs are best suited for one or more specific sleep stages and for the awake patient state.

Memory 72 may include instructions for operating user interface 76, telemetry module 74 and managing power source 78. Memory 72 may also store any therapy data retrieved from IMD 16 during the course of therapy. The clinician may use this therapy data to determine the progression of the patient condition in order to predict future treatment. Memory 72 may include any volatile or nonvolatile memory, such as RAM, ROM, EEPROM or flash memory. Memory 72 may also include a removable memory portion that may be used to provide memory updates or increases in memory capacities. A removable memory may also allow sensitive patient data to be removed before programmer 14 is used by a different patient.

Memory 72 may be considered, in some examples, a non-transitory computer-readable storage medium comprising instructions that cause one or more processors, such as, e.g., processor 70 or processor 50 (FIG. 2), to implement one or more of the example techniques described in this disclosure. The term "non-transitory" may indicate that the storage medium is not embodied in a carrier wave or a propagated signal. However, the term "non-transitory" should not be interpreted to mean that memory 72 is non-movable. As one example, memory 72 may be removed from programmer 14, and moved to another device. In certain examples, a non-transitory storage medium may store data that can, over time, change (e.g., in RAM).

Wireless telemetry in programmer 14 may be accomplished by RF communication or proximal inductive interaction of external programmer 14 with IMD 16. This wireless communication is possible through the use of telemetry module 74. Accordingly, telemetry module 74 may be similar to telemetry module 56 of IMD 16. In alternative examples, programmer 14 may be capable of infrared communication or direct communication through a wired connection. In this manner, other external devices may be capable of communicating with programmer 14 without needing to establish a secure wireless connection.

Power source 78 delivers operating power to the components of programmer 14. Power source 78 may include a battery and a power generation circuit to produce the operating power. In some examples, the battery may be rechargeable to allow extended operation. Recharging may be accomplished by electrically coupling power source 78 to a cradle or plug that is connected to an alternating current (AC) outlet. In addition, recharging may be accomplished through proximal inductive interaction between an external charger and an inductive charging coil within programmer 14. In other examples, traditional batteries (e.g., nickel cadmium or lithium ion batteries) may be used. In addition, programmer 14 may be directly coupled to an alternating current outlet to operate. Power source 78 may include circuitry to monitor power remaining within a battery. In this manner, user interface 76 may provide a current battery level indicator or low battery level indicator when the battery needs to be replaced or recharged. In some cases, power source 78 may be capable of estimating the remaining time of operation using the current battery.

As described above, to treat or manage RBD, IMD 16 may deliver electrical stimulation therapy to brain 13 of patient 12 when patient 12 is determined to be in a REM sleep stage. The electrical stimulation delivered to patient 12 by IMD 16 may be configured to inhibit the physical movement of patient 12 associated with RBD while patient 12 is in a REM sleep stage. In some instances, patient 12 may involuntarily move his/her limbs during the REM sleep stage or have other periodic physical movements caused by RBD. The physical activity of patient 12 may be disruptive to the patient's sleep, as well as to others around patient 12 when patient 12 is in the REM sleep stage. Accordingly, upon detecting a sleep stage associated with the REM sleep stage, delivery of electrical stimulation to brain 13 via electrodes 22 may minimize the movement of patient 12. By reducing or preventing physical movement of patient 12 during the REM sleep stage, the quality of the patient's sleep may improve and may also reduce the danger posed by patient 12 to himself/herself from physical movements associated with RBD.

Figure 4:
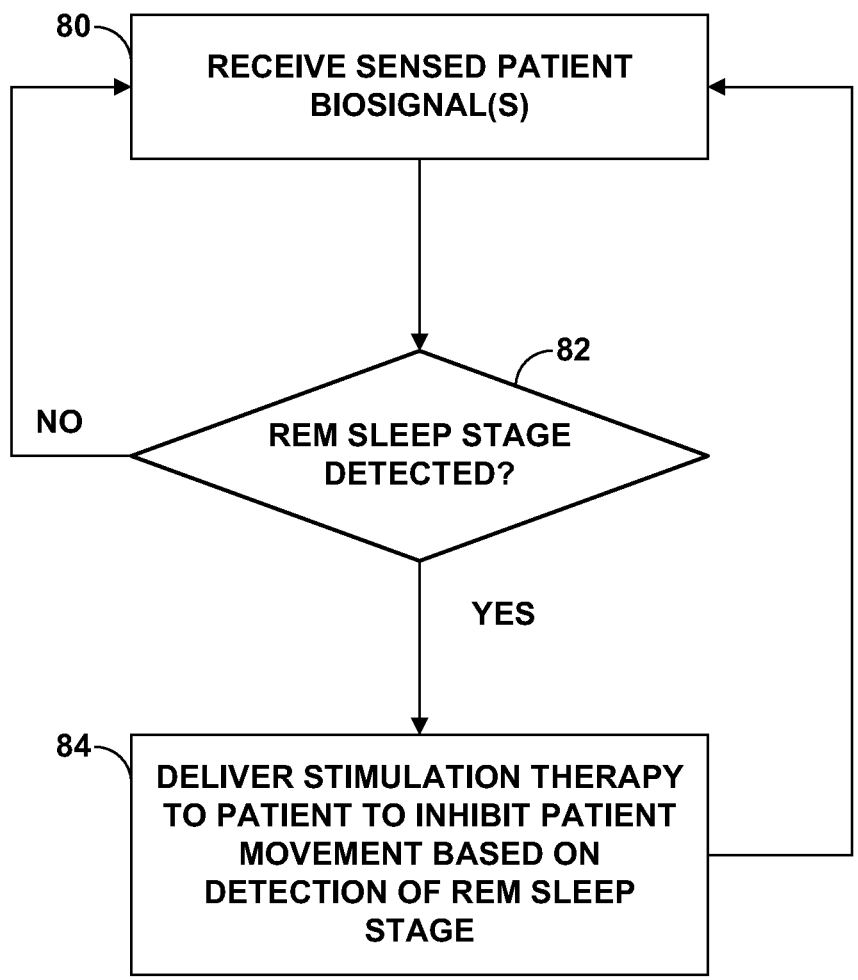
FIG. 4 is a flow diagram illustrating an example technique for delivering electrical stimulation therapy from a medical device to the brain of a patient to treat RBD.
Figure 5:
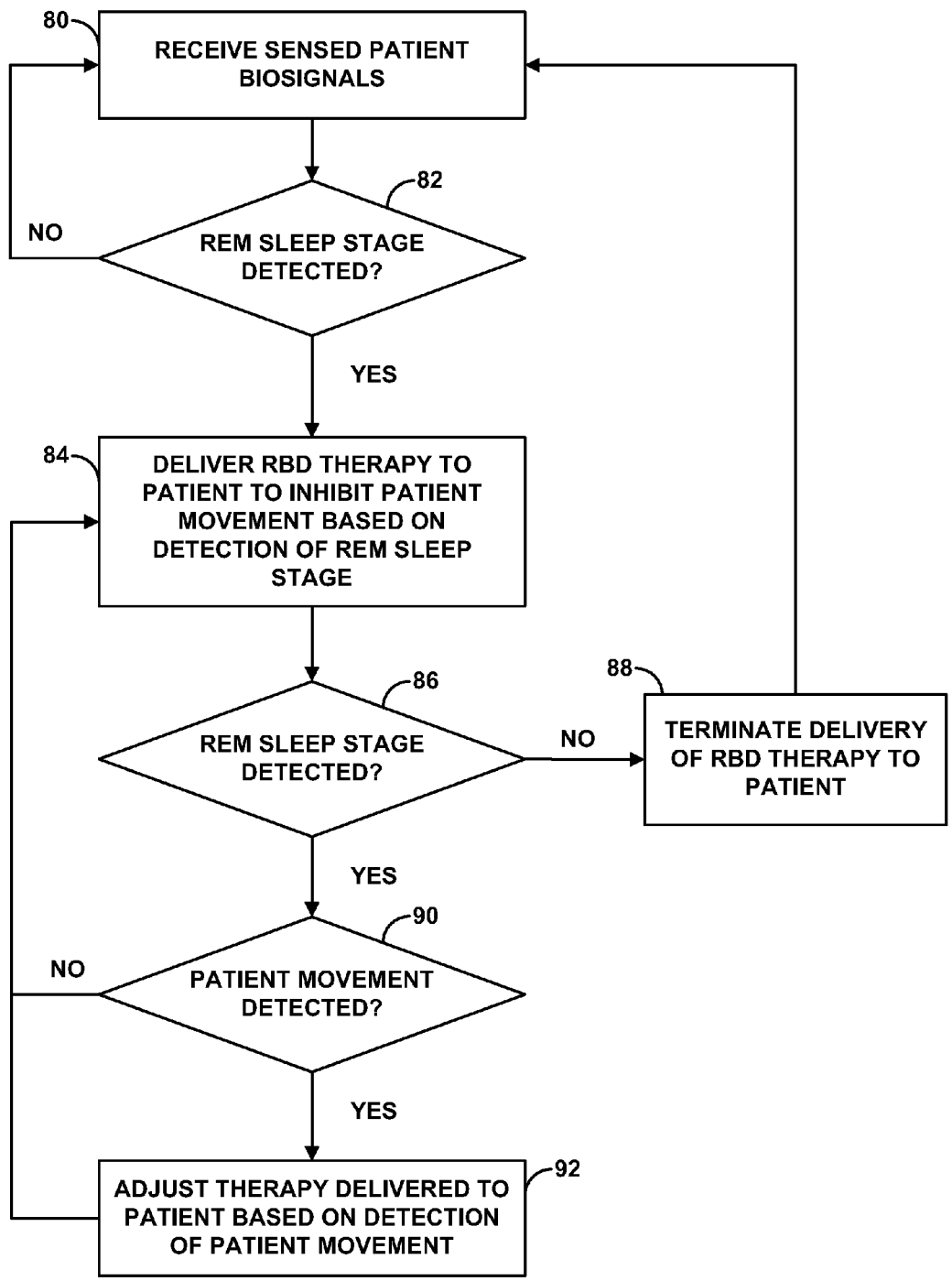
FIG. 5 is a flow diagram illustrating another example technique for delivering electrical stimulation therapy from a medical device to the brain of a patient to treat RBD.

FIG. 4 is a flow diagram illustrating an example technique for delivering electrical stimulation therapy from a medical device to the brain of a patient to treat RBD. For ease of illustration, the example techniques of FIGS. 4 and 5 are described primarily with regard to the delivery of therapy to patient 12 from DBS system 10. However, such an example technique may be employed in any suitable medical device system. Moreover, while the detection of RBD, control of therapy delivery to brain 13 of patient 12 from IMD 16, and other functionality is described primarily with reference to processor 50 of IMD 16, in other examples, a processor of another device, such as processor 70 of programmer 14, may perform one or more of such steps in combination with, or in lieu of, processor 50 in accordance with some examples of the disclosure. For example, while processor 50 of IMD 16 is described below as analyzing sensed biosignals of patient 12 to determine whether or not patient 12 is in a REM sleep stage, in some examples, one or more processors of another device, such as processor 70 of programmer 14 may perform all or a portion of such analysis.

As shown in FIG. 4, processor 50 receives one or more sensed biosignals indicative of activity within brain 13 of patient 12 (80), e.g., from sensing module 55 (FIG. 2) or a separate sensing module that senses the biosignal within brain 13 of patient 12. In some examples, processor 50 may continuously receive the biosignal (80) from sensing module 55 or at periodic intervals, which may be set by a clinician. For example, processor 50 may periodically interrogate sensing module 55 to receive the biosignal (80). In other examples, processor 50 may receive the biosignals from sensing module 55 (80) only after processor 50 has determined that patient 12 is in a sleep state (rather than in an "awake" state).

Based on the received biosignals of patient 12 (80), processor 50 may determine whether or not patient 12 is in a REM sleep state (82). If processor 50 determines that patient 12 is not in a REM sleep stage (82), processor 50 continues to monitor sensed biosignals of patient 12 to determine when patient 12 occupies a REM sleep stage. In some examples, processor 50 may determine that patient 12 is not in a REM sleep stage by determining that patient 12 instead occupies another sleep stage or is in an "awake" state.

Alternatively, if processor 50 determines that patient 12 is in a REM sleep stage (82), processor 50 may control stimulation generator 54 to generate and deliver electrical stimulation therapy to brain 13 of patient 12 to inhibit physical movement of patient 12 (84). In general, the therapy delivered to patient 12 may treat symptoms of RBD by reducing or preventing the uncontrolled physical movements of patient 12 that are associated with RBD during REM sleep. As described above, in some examples, processor 50 may control the delivery of therapy to brain 13 of patient 12 in a manner that causes muscle rigidity in patient 12 to effectively hold patient 12 still during the time when patient is susceptible to uncontrolled movements during REM sleep due to RBD. In other examples, processor 50 may control delivery of electrical stimulation therapy to brain 13 of patient 12 in a manner that causes relaxed muscle tone of patient 12 to inhibit patient movement. In still other examples, processor 50 may control delivery of electrical stimulation therapy to brain 13 of patient 12 to cause atonia or akinesia in patient 12. In each case, the electrical stimulation therapy delivered to brain 13 of patient 12 by IMD 16 may temporarily reduce or prevent the uncontrolled physical movement of patient 12 associated with RBD during REM sleep. In some examples, such as those in which patient 12 is exhibiting uncontrolled movement associated with RBD despite the delivery of electrical stimulation therapy configured to inhibit patient movement, processor 50 may control the delivery of stimulation therapy to patient 12 in a manner that terminates the REM sleep stage of patient 12.

Processor 50 may substantially immediately control stimulation generator 54 to begin delivering therapy to brain 13 of patient 12 once processor determines that patient 12 occupies a REM sleep state (82). In other examples, a time delay may be employed such that processor 50 delays the delivery of electrical stimulation to patient 12. Such a time delay may be selected and stored in memory 52 to correspond to the period of time between patient 12 entering a REM sleep state and when uncontrolled movement of patient 12 due to RBD is typically experienced by patient 12. In other examples, processor 50 may delay delivery of therapy to patient 12 until physical movement of patient 12 is detected, e.g., via one or more accelerometers devices of sensing module 55, when patient 12 is in a REM sleep stage. That is, once physical movement of patient 12 is detected in combination with processor 50 determining patient 12 is in a REM sleep stage based on the sensed biosignal(s) of patient 12, processor 50 may control stimulation generator 54 to generate and deliver electrical stimulation to brain 13 to inhibit physical movement of patient 12, as described herein. In this manner, processor 50 may withhold delivery of stimulation throughout the entire REM sleep stage of patient in instances in which uncontrolled movement associated with RBD is not experienced by patient 12 during the respective REM sleep stage.

In the example of FIG. 4, processor 50 may control the delivery of electrical stimulation therapy to brain 13 of patient 12 to treat RBD (84) until processor 50 determines that patient 12 is no longer in a REM sleep stage based on the sensed biosignals of patient 12 (82). In some examples, processor 50 may instead control the delivery of stimulation therapy to patient 12 for a preset period of time stored in memory 52. For example, using programmer 14, a clinician may select a period of time that IMD 16 delivers electrical stimulation therapy to patient 12 upon detecting that patient 12 is in a REM sleep stage (84). Such a period of time may generally correspond to the average or longest amount of time between patient 12 entering a REM sleep stage and subsequently exiting the REM sleep stage. Such a time period may be patient specific (e.g., as determined during a trial or observation period) or may be based on REM sleep stage period observed in other patients. In some examples, processor 50 may control stimulation generator 54 to deliver electrical stimulation therapy to patient 12 for a time between approximately 10 minutes and approximately 60 minutes after processor 50 determines that patient 12 is in a REM sleep stage based on the sensed biosignals (80). In still other examples, processor 50 may continue the delivery of electrical stimulation therapy to patient 12 to treat RBD until patient 12 enters an "awake" state (i.e., wakes-up from sleeping).

During the time that IMD 16 delivers stimulation therapy to patient 12 to treat one or more symptoms of RBD, processor 50 may control stimulation generator 54 to generate and deliver electrical stimulation therapy to brain 13 of patient 12 to inhibit physical movement of patient 12. Processor 50 may control the electrical stimulation therapy according to one or more therapy programs stored in memory 52 or memory 72 (FIG. 3) defining stimulation therapy parameters. Processor 50 may control the electrical stimulation therapy such that the stimulation therapy is delivered to brain 13 on a substantially continuous basis, e.g., throughout substantially the entire time period patient 12 is determined to be in a REM sleep stage, or may cause the stimulation therapy to be delivered to brain 13 of patient 12 on a periodic basis after patient 12 is determined to be in a REM sleep stage. In some examples, IMD 16 may deliver therapy in an on-demand fashion based on physical movement of patient 12. For example, processor 50 may control stimulation generator 55 to deliver electrical stimulation to brain 13 of patient 12 for a relatively short period of time when physical movement of patient 12 is detected in combination with patient 12 being in a REM sleep stage to stop of the physical movement of patient 12. Such a process may be repeated throughout the time period that patient 12 occupies a REM sleep stage for each instance of physical movement detected by processor 50.

As described above, in some cases, IMD 16 may deliver electrical stimulation therapy to brain 13 of patient 12 to treat one or more disorders besides that of RBD. For example, IMD 16 may be configured to deliver electrical stimulation to brain 13 of patient 12 to treat one or more symptoms of Parkinson's disease, which may be correlated in some cases with patients having RBD. In such cases, if IMD 16 is actively delivering electrical stimulation to brain 13 of patient 12 to treat another patient disorder, upon determining that patient 12 is in a REM sleep stage, processor 50 may adjust one or more stimulation therapy parameters (e.g., by changing therapy programs) of the electrical stimulation therapy to therapy that effectively treats RBD. In some examples, the therapy being delivered by IMD 16 to treat the other patient disorder may be temporally suspended in favor of the stimulation for treating RBD. In other examples, processor 50 may control the delivery of stimulation therapy to brain 13 to treat both patient disorders, e.g., by controlling the delivery of respective stimulation therapies to brain 13 in an interleaved fashion.

As described above, processor 50 may determine patient 12 is in a REM sleep stage based on sensed biosignal(s) of patient 12 (80). In some examples, processor 50 may be configured to detect additional sleep stage of patient 12 beyond that of a REM sleep stage based on sensed biosignals of patient 12. In one example, processor 50 may determine a REM sleep stage and/or other sleep stages of patient based on a frequency band characteristic of the biosignal that is indicative of activity within brain 13 of patient 12. An example technique for determining a sleep stage of patient, including a REM sleep stage, based on a frequency band characteristic of the biosignal is described in U.S. Patent Application Publication No. 2009/0192556 by Wu et al. (published on Jul. 30, 2009), which is entitled, "SLEEP STAGE DETECTION" and is incorporated herein by reference in its entirety.

In examples in which processor 50 determines the sleep stage of patient 12 and, in particular, whether patient 12 is in a REM sleep stage, processor 50 may determine a frequency band characteristic of the received biosignal (80) using any suitable technique. The frequency characteristic may include, for example, at least one of a power level (or energy) within one or more frequency bands of the biosignal, a ratio of the power level in two or more frequency bands, a correlation in change of power between two or more frequency bands, or a pattern in the power level of one or more frequency bands over time. In one example, sensing module 55 may include an amplifier that amplifies a received biosignal and a bandpass or a low pass filter that filters the monitored biosignal to extract one or more selected frequency bands of the biosignal. The extracted frequency bands may be selected based on the frequency band that is revealing of the one or more sleep stages that are being detected. Processor 55 may then determine the frequency characteristic based on the extracted frequency band component of the biosignal.

As described in U.S. Patent Application Publication No. 2009/0192556 by Wu et al., different frequency bands are associated with different activity in brain 13. It is believed that some frequency band components of a biosignal from within brain 13 may be more revealing of particular sleep stages than other frequency components. One example of the frequency bands is shown in Table 2:

TABLE 2

| Frequency bands | |
|---|---|
| Frequency (f) Band Hertz (Hz) | Frequency Information |
| f < 5 Hz | δ (delta frequency band) |
| 5 Hz ≤ f ≤ 10 Hz | α (alpha frequency band) |
| 10 Hz ≤ f ≤ 30 Hz | β (beta frequency band) |
| 50 Hz ≤ f ≤ 100 Hz | γ (gamma frequency band) |
| 100 Hz ≤ f ≤ 200 Hz | high γ (high gamma frequency band) |

The frequency ranges for the frequency bands shown in Table 2 are merely examples. The frequency ranges may differ in other examples. For example, another example of frequency ranges for frequency bands are shown in Table 3:

TABLE 3

| Frequency bands | |
|---|---|
| Frequency (f) Band Hertz (Hz) | Frequency Information |
| f < 5 Hz | δ (delta frequency band) |
| 5 Hz ≤ f ≤ 8 Hz | q (theta frequency band) |
| 8 Hz ≤ f ≤ 12 Hz | α (alpha frequency band) |
| 12 Hz ≤ f ≤ 16 Hz | s (sigma or low beta frequency band) |
| 16 Hz ≤ f ≤ 30 Hz | High β (high beta frequency band) |
| 50 Hz ≤ f ≤ 100 Hz | γ (gamma frequency band) |
| 100 Hz ≤ f ≤ 200 Hz | high γ (high gamma frequency band) |

Processor 50 may select a frequency band for determining the patient sleep stage using any suitable technique. In one example, the clinician may select the frequency band based on information specific to patient 12 or based on data gathered from more than one patient 12. The frequency bands that are useful for distinguishing between two or more different patient sleep stages or otherwise determining a patient sleep stage based on a biosignal from brain 13 may differ between patients. In some examples, a clinician may calibrate the frequency ranges to a specific patient based on, for example, a sleep study. During the sleep study, the clinician may monitor a biosignal and determine which, if any, frequency bands or ratio of frequency bands exhibit a characteristic that helps to detect a sleep stage and/or distinguish between different sleep stages.

As described above, processor 50 may determine a REM sleep stage or other sleep stage based on the frequency characteristic of the biosignal (80). In some cases, processor 50 may compare the frequency characteristic to one or more threshold values in order to determine the respective sleep stage. In other examples, processor 50 may compare a trend in the power level within a frequency band of the biosignal over time to a template in order to determine the sleep stage. In some examples, the REM sleep stage can be determined by the detection of one or more specific waveforms indicative of a REM sleep stage, which may include rapid eye movement, one or more "saw-tooth" wave forms from an EEG signal, and Ponto-geniculo-occipital (PGO) waves, e.g., generated from LFP within the PPN of patient 12.

In addition to or instead of determining whether or not patient 12 is in a REM sleep state based on sensed biosignals of patient 12 (80), processor 50 may also determine that patient 12 is in a REM sleep stage using one or more suitable techniques. In some examples, IMD 16 my monitor the eye movement of patient 12 using EMG signals sensed via sensing module 55 or EEG/EOG signals to detect rapid movement of the eyes of patient 12 indicative of a REM sleep stage. In some examples, processor 80 may monitor the body temperature of patient 12 at one or more locations (e.g., within brain 13) via sensing module 55 to detect when patient 12 is in a REM sleep stage. In some examples, fluctuations of body temperature may be indicative of a REM sleep stage and relatively constant body temperature may be indicative of sleep stages other than the REM sleep stage (e.g., sleep stages 1-4). In such an example, processor 50 may determine that patient 12 is in a REM sleep stage when temperature fluctuations indicative of a REM sleep stage are sensed.

Processor 50 may determine that patient 12 is in a REMS sleep stage in advance of patient 12 actually entering a REM sleep stage. In some examples, processor 50 may identify one or more indicators present prior to patient 12 entering a REM sleep stage. For example, processor 50 may identify when patient 12 is in a light sleep stage (e.g., sleep stage 1 or 2) rather than in a deep sleep stage (e.g., sleep stage 3 or 4). As patient 12 may be more likely to enter a REM sleep stage directly following a light sleep stage as compared to a deep sleep stage, processor 50 may initiate the delivery of therapy to treat or manage RBD when processor 50 determines that patient 12 is in a light sleep stage and withhold such stimulation when patient 12 is in a deep sleep stage. Any suitable means of detecting such sleep stages may be utilized. In some examples, high amplitude beta activity (12-26 Hz) may be indicative of patient 12 occupying a light sleep stage while high amplitude delta activity (0.5-4 Hz) may be indicative of patient 12 occupying a deep sleep stage. Processor 50 may monitor for such indicators via sensing module 55.

In some examples, IMD 16 may deliver therapy that overlaps one or more other sleep stages prior to or following a REM sleep stage. For example, processor 50 may initiate the delivery of therapy to inhibit movement of patient 12 to treat RBD when processor 50 determines that patient 12 occupies a light sleep stage in anticipation of patient 12 occupying a REM sleep stage in the near future. However, the amount of overlap may be relatively slight in some examples to protect against inhibiting patient movement attendant to such light sleep stages.

In some examples, IMD 16 may identify temporal patterns of patient 12 to identify a time period that patient 12 has a relatively high probability of being in a REM sleep stage. In some examples, based on patient history, processor 50 may identify periods of time that patient 12 generally is asleep and period of time when patient 12 is generally awake during a day. Processor 50 may only actively monitor for a REM sleep stage, e.g., based on sensed biosignals, during those periods patient 12 is determined to generally be asleep based on patient history. Other temporal sleep patterns may be identified to assist in identifying time periods for IMD 16 to deliver therapy to patient 12 to treat RBD as described in this disclosure.

Processor 50 may be configured to monitor the sensed biosignals and/or other parameters indicative of a REM sleep stage on any suitable basis (80). In some examples, processor 50 may monitor the sensed biosignals and/or other parameters to determine when patient 12 is in a REM sleep stage on a substantially continuous basis. In other examples, processor 50 may only monitor for a REM sleep stage when patient 12 is determined to be sleeping. As described above, patient 12 may be determined to be in a sleep state based on sensed biosignals, and/or based on patient occupying a lying posture state (e.g., as determined with one or more accelerometer sensors) for a period of time indicative of patient sleeping. In some examples, processor 50 may be configured to actively monitor for a REM sleep stage of patient 12 based on time of day, e.g., during one or more times during the day that patient 12 typically sleeps.

In instances in which processor 50 is configured to actively monitor for a REM sleep stage of patient 12 when patient 12 is determined to be sleeping, processor 50 may detect patient is asleep based on sensed biosignals of patient 12. In some examples, processor 50 of IMD may confirm that patient 12 is asleep based on a physiological parameter of patient 12 other than a sensed biosignal or may use such a sleep detection technique in place of a technique that detects a patient is asleep based on sensed patient biosignals. In one example, processor 50 of IMD 16 may determine values of one or more sleep metrics that indicate a probability of a patient being asleep based on the current value of one or more physiological parameters of the patient, as described in commonly-assigned U.S. Patent Application Publication No. 2005/0209512 by Heruth et al., entitled "DETECTING SLEEP," which was filed on Apr. 15, 2004. U.S. Patent Application Publication No. 2005/0209512 is incorporated herein by reference in its entirety.

As described in U.S. Patent Application Publication No. 2005/0209512, a sensor that is incorporated with IMD 16, or, in some examples, a separate sensor, may generate a signal as a function of at least one physiological parameter of a patient that may discernibly change when the patient is asleep. Examples of physiological parameters that may indicate a sleep stage include, for example, activity level, posture, heart rate, respiration rate, respiratory volume, blood pressure, blood oxygen saturation, partial pressure of oxygen within blood, partial pressure of oxygen within cerebrospinal fluid, muscular activity, core temperature, arterial blood flow, and galvanic skin response. In some examples, processor 50 of IMD 16 may determine a value of a sleep metric that indicates a probability of the patient being asleep based on a physiological parameter. In particular, processor 50 may apply a function or look-up table to the current value and/or variability of the physiological parameter to determine the sleep metric value. Processor 50 may compare the sleep metric value to a threshold value to determine whether the patient is asleep. In some examples, the probability may be more than just an indication of "sleep state" or "awake state" but may include an indication of the probability, e.g., between 1% to about 100%, that patient 12 is in a sleep state.

FIG. 5 is a flow diagram illustrating another example technique for delivering electrical stimulation therapy from a medical device to the brain of a patient to treat RBD. Similar to that of FIG. 4, processor 50 may receive sensed patient biosignals (80) and determine whether or not patient 12 is in a REM sleep state (82). If processor 50 determines that patient 12 is in a REM sleep state based on the received patient biosignal(s) (82), processor 50 may control stimulation generator 54 to generate and deliver electrical stimulation to brain 13 of patient 12 to inhibit the physical movement of patient 12 (84), as described in the disclosure, to reduce or prevent uncontrolled movement of patient associated with RBD while patient 12 is in a REM sleep stage.

In the example of FIG. 5, IMD 16 may continue to deliver electrical stimulation therapy to patient 12 to treat RBD until processor 50 determines that patient 12 is no longer in a REM sleep stage (86), e.g., as indicated by sensed patient biosignal(s). If patient 12 is determined to no longer be in the REM sleep stage, processor 50 may terminate the delivery of RBD stimulation therapy to patient 12 (88). Until that time, while IMD 16 delivers electrical stimulation therapy to patient 12 to treat RBD, processor 50 may monitor the physical movement of patient via sensing module 55 (90). For example, as described above, sensing module 55 may include one or more accelerometer sensors which generate a signal indicative of patient movement or lack thereof, and processor 50 may analyze such sensor information to determine whether or not patient 12 is moving. Alternatively or additionally, processor 50 may analyze an EMG signal sensed via sensing module 55 to monitor physical movement of patient 12 based on the sensed muscle tone of patient 12.

If processor 50 does not detect physical movement or detects only a nominal amount of physical movement of patient 12 while IMD 16 is delivering electrical stimulation therapy to patient 12 to treat RBD (90), processor 50 may continue to deliver electrical stimulation therapy according to the selected stimulation parameters and tissue site(s) of brain 13 currently being employed. In such an example, the lack of physical movement of patient 12 may indicate that the electrical stimulation therapy delivery by IMD 16 to patient 12 is effective in reducing or preventing uncontrolled movement associated with RBD.

Conversely, if processor 50 detects any physical movement of patient 12 (90), processor 50 may adjust the electrical stimulation therapy being delivered to patient 12. In some examples, processor 50 may be configured to allow for a nominal amount of physical movement before adjusting the electrical stimulation being delivered to patient 12. For example, processor 50 may disregard physical movement of the eyes of patient 12, including the high frequency movement of the eyes exhibited during a REM sleep stage. Processor 50 may also disregard physical movement that has a relatively slow onset and/or is aperiodic in occurrences. In some examples, processor 50 may disregard physical movement associated with other disorders of patient 12 which are different than that of the physical movement associated with RBD and the target of the therapy delivered to patient 12 during REM sleep. For example, for an instance in which patient 12 has Parkinson's disease as well as RBD, processor 50 may disregard tremors or relatively low amplitude, high frequency movement of patient which may be associated with Parkinson's disease.

To adjust the therapy being delivered to patient 12 (92), processor 50 may modify the value of one or more electrical stimulation therapy parameters defining the current electrical stimulation therapy, e.g., by modifying one or more values defined by a selected therapy program or selecting a new therapy program stored in memory 52. Additionally or alternatively, processor 50 may adjust the stimulation therapy upon detection of patient movement (90) by changing the tissue site to which electrical stimulation is being delivered. In one example, processor 50 may change from controlling delivery of electrical stimulation configured to cause rigidity of patient to delivery of therapy configured to cause relaxation of muscle tone in patient 12, or vice versa. Processor 50 may continue to monitor for physical movement of patient and adjust the stimulation therapy being delivered to patient 12 as needed until processor 50 determines patient 12 no longer is in a REM sleep stage. As patient movement may be an indicator of electrical stimulation therapy that is ineffective in treating the one or more symptoms of RBD, such a technique may be used to maintain effective delivery of electrical stimulation therapy to patient 12 to manage or treat RBD when patient 12 is in a REM sleep stage.

The techniques described in this disclosure, including those attributed to programmer 14, IMD 16, or various constituent components, may be implemented, at least in part, in hardware, software, firmware or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices or other devices. The term "processor" or "processing circuitry" may generally refer to any of the foregoing logic circuitry, alone or in combination with other logic circuitry, or any other equivalent circuitry.

Such hardware, software, firmware may be implemented within the same device or within separate devices to support the various operations and functions described in this disclosure. While the techniques described herein are primarily described as being performed by processor 50 of IMD 16 and/or processor 70 of programmer 14, any one or more parts of the techniques described herein may be implemented by a processor of one of IMD 16, programmer 14, or another computing device, alone or in combination with each other.

In addition, any of the described units, modules or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed to support one or more aspects of the functionality described in this disclosure.

Various examples have been described. These and other examples are within the scope of the following claims.

The invention claimed is:

1. A method comprising:
    determining a patient is in a rapid eye movement (REM) sleep stage; and
    controlling a therapy module to deliver therapy to the patient based on the determination that the patient is in the REM sleep stage, wherein the therapy is configured to inhibit movement of the patient during the determined REM sleep stage;
    detecting, while the therapy is being delivered to the patient during the determined REM sleep stage, at least one of the movement of the patient or the muscle tone of the patient via a sensing module; and
    adjusting the therapy delivered to the patient via the therapy module based on the at least one of the movement of the patient or the muscle tone of the patient detected via the sensing module, wherein at least one of the determining, controlling, detecting, or adjusting is performed using one or more processors.

2. The method of claim 1, wherein determining the patient is in the REM sleep stage comprises:
    sensing a biosignal that is indicative of activity within a brain of the patient; and
    determining the REM sleep stage based on the sensed biosignal.

3. The method of claim 2, wherein the sensed biosignal comprises a bioelectrical brain signal generated from at least one of local field potentials (LFP) within a brain of the patient, an electroencephalogram (EEG) signal, or an electrocorticogram (ECoG) signal.

4. The method of claim 1, wherein the therapy comprises electrical stimulation therapy, and wherein adjusting the electrical stimulation therapy delivered to the patient comprises one of terminating the electrical stimulation or modifying one or more stimulation therapy parameters.

5. The method of claim 4, wherein the one or more stimulation therapy parameters comprise pulse rate, pulse width, pulse amplitude, electrode polarity, or electrode combination.

6. The method of claim 1, wherein controlling the therapy module to deliver the therapy to the patient comprises controlling the therapy module to deliver electrical stimulation therapy to a brain of the patient.

7. The method of claim 6, wherein controlling the therapy module to deliver the electrical stimulation therapy to the brain comprises controlling the therapy module to deliver electrical stimulation to at least one of a globus pallidus pars interna (GPi), subthalamic nucleus (STN), striatum, pallidum, or substantia nigra of the brain.

8. The method of claim 7, wherein controlling the therapy module to deliver the electrical stimulation therapy to the at least one of a globus pallidus pars interna (GPi), subthalamic nucleus (STN) striatum, pallidum, or substantia nigra comprises controlling the therapy module to deliver electrical stimulation having a frequency of between approximately 8 Hz and 30 Hz to the at least one of the globus pallidus pars interna (GPi), subthalamic nucleus (STN), striatum, pallidum, or substantia nigra of the brain.

9. The method of claim 6, wherein controlling the therapy module to deliver the electrical stimulation therapy to the brain comprises controlling the therapy module to deliver electrical stimulation to a midbrain nuclei of the brain.

10. The method of claim 9, wherein controlling the therapy module to deliver the electrical stimulation therapy to the midbrain nuclei comprises controlling the therapy module to deliver electrical stimulation having a frequency of between approximately 80 Hz and 200 Hz to the midbrain nuclei of the brain.

11. The method of claim 1, further comprising:
subsequently determining that the patient is not in the REM sleep stage; and
terminating the therapy delivered to the patient based on the determination that the patient is not in the REM sleep stage.

12. The method of claim 1, wherein controlling the therapy module to deliver the therapy to the patient comprises controlling the therapy module to deliver electrical stimulation therapy to the patient.

13. The method of claim 12, wherein controlling the therapy module to deliver the electrical stimulation therapy to the patient comprises at least one of initiating delivery of electrical stimulation or adjusting one or more stimulation therapy parameters of the stimulation therapy.

14. The method of claim 1, wherein controlling the therapy module to deliver the therapy to the patient comprises controlling the therapy module to deliver electrical stimulation to at least one of a brain, muscle, or spinal cord of the patient.

15. The method of claim 1, wherein controlling the therapy module to deliver the therapy to the patient comprises controlling the therapy module to deliver a therapeutic agent to the patient.

16. A system comprising:
means for determining a patient is in a rapid eye movement (REM) sleep stage; and
means for delivering therapy to the patient based on the determination that the patient is in the REM sleep stage by the means for determining, wherein the therapy is configured to inhibit movement of the patient during the determined REM sleep stage;
means for detecting, while the therapy is being delivered to the patient during the determined REM sleep stage, at least one of the movement of the patient or a muscle tone of the patient; and
means for adjusting the therapy delivered to the patient by the means for delivering based on the at least one of the movement of the patient or the muscle tone of the patient detected by the means for detecting.

17. A system comprising:
a sensing module configured to detect at least one of movement of a patient or muscle tone of the patient;
a therapy module; and
a processor configured to determine the patient is in a rapid eye movement (REM) sleep stage, control the therapy module to deliver therapy to the patient based on the determination, wherein the therapy is configured to inhibit movement of the patient during the determined REM sleep stage, detect, while the therapy is being delivered to the patient during the determined REM sleep stage, the at least one of the movement of the patient or the muscle tone of the patient via the sensing module, and adjust the therapy delivered to the patient via the therapy module based on the at least one of the movement of the patient or the muscle tone of the patient detected via the sensing module.

18. The system of claim 17, wherein the sensing module comprises a first sensing module, wherein the processor is configured to determine the patient is in the REM sleep stage by at least:
sensing, via a second sensing module, a biosignal that is indicative of activity within a brain of the patient; and
determining the REM sleep stage based on the sensed biosignal.

19. The system of claim 18, wherein the sensed biosignal comprises a bioelectrical brain signal generated from at least one of local field potentials (LFP) within a brain of the patient, an electroencephalogram (EEG) signal, or an electrocorticogram (ECoG) signal.

20. The system of claim 17, wherein the therapy delivered by the therapy module comprises electrical stimulation therapy, and wherein the processor is configured to adjust the electrical stimulation therapy delivered to the patient by at least one of terminating the electrical stimulation or modifying one or more stimulation therapy parameters.

21. The system of claim 20, wherein the one or more stimulation therapy parameters comprise pulse rate, pulse width, pulse amplitude, electrode polarity, or electrode combination.

22. The system of claim 17, wherein the processor is configured to control the therapy module to deliver therapy to the patient by at least controlling the therapy module to deliver electrical stimulation therapy to a brain of the patient.

23. The system of claim 22, wherein the processor is configured to control the therapy module to deliver the electrical stimulation therapy to the brain of the patient by at least controlling the therapy module to deliver electrical stimulation to at least one of a globus pallidus pars interna (GPi), subthalamic nucleus (STN), striatum, pallidum, or substantia nigra of the brain.

24. The system of claim 23, wherein the processor is configured to control the electrical stimulation delivered to the at least one of the globus pallidus pars interna (GPi), subthalamic nucleus (STN), striatum, pallidum, or substantia nigra of the brain to have a frequency of between approximately 8 Hz and 30 Hz.

25. The system of claim 22, wherein the processor is configured to control the therapy module to deliver electrical stimulation therapy to the brain of the patient by at least controlling the therapy module to deliver of electrical stimulation to a midbrain nuclei of the brain.

26. The system of claim 25, wherein the processor is configured to control the electrical stimulation delivered to the midbrain nuclei to have a frequency of between approximately 80 Hz and 200 Hz.

27. The system of claim 17, wherein the processor is configured to subsequently determine that the patient is not in the REM sleep stage, and terminate the therapy delivered to the patient based on the determination that the patient is not in the REM sleep stage.

28. The system of claim 17, wherein the processor is configured to control the therapy module to deliver the therapy by at least controlling the therapy module to deliver electrical stimulation therapy to the patient.

29. The system of claim 28, wherein the processor is configured to control the therapy module to deliver the electrical stimulation therapy to the patient by at least one of initiating delivery of electrical stimulation or adjusting one or more stimulation therapy parameters of the stimulation therapy.

30. The system of claim 17, wherein the processor is configured to control the therapy module to deliver therapy to the patient by at least controlling the therapy module to deliver electrical stimulation to at least one of a brain, muscle, or spinal cord of the patient.

31. The system of claim 17, wherein the processor is configured to control the therapy module to deliver therapy by at least controlling the therapy module to deliver a therapeutic agent to the patient.

32. The system of claim 17, wherein the therapy is configured to relax the muscle tone of the patient to inhibit the movement of the patient during the determined REM sleep stage.

33. The system of claim 17, wherein the processor is configured to detect the muscle tone of the patient via the sensing module while the therapy is being delivered to the patient during the determined REM sleep stage, and adjust the therapy delivered to the patient via the therapy module based on the detected muscle tone of the patient.

34. A system comprising:
a sensing module configured to detect at least one of movement of a patient or muscle tone of the patient;
a therapy module configured to deliver therapy to the patient; and
a processor configured to determine the patient is in a rapid eye movement (REM) sleep stage, control the therapy module to deliver the therapy to the patient based on the determination, wherein the therapy is configured to relax muscle tone of the patient to inhibit the movement of the patient during the determined REM sleep stage, detect, while the therapy is being delivered to the patient during the determined REM sleep stage, the at least one of the movement of the patient or the muscle tone of the patient via the sensing module, and adjust the therapy delivered to the patient via the therapy module based on the at least one of the movement of the patient or the muscle tone of the patient detected via the sensing module.

* * * * *